(12) United States Patent
Dugas et al.

(10) Patent No.: US 12,011,508 B2
(45) Date of Patent: Jun. 18, 2024

(54) METHODS AND DEVICES FOR REDUCING VASCULAR SMOOTH MUSCLE CELL PROLIFERATION

(71) Applicant: Board of Supervisors of Louisiana State University and Agricultural and Mechanical College, Baton Rouge, LA (US)

(72) Inventors: Tammy Renee Dugas, Baton Rouge, LA (US); Cristina Sabliov, Baton Rouge, LA (US); Carlos Astete, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 902 days.

(21) Appl. No.: 16/965,078

(22) PCT Filed: Feb. 1, 2019

(86) PCT No.: PCT/US2019/016302
§ 371 (c)(1),
(2) Date: Jul. 27, 2020

(87) PCT Pub. No.: WO2019/152811
PCT Pub. Date: Aug. 8, 2019

(65) Prior Publication Data
US 2021/0106728 A1    Apr. 15, 2021

Related U.S. Application Data

(60) Provisional application No. 62/625,026, filed on Feb. 1, 2018.

(51) Int. Cl.
| | |
|---|---|
| *A61K 9/51* | (2006.01) |
| *A61K 31/05* | (2006.01) |
| *A61K 31/366* | (2006.01) |
| *A61L 29/08* | (2006.01) |
| *A61L 29/16* | (2006.01) |
| *A61M 25/10* | (2013.01) |
| *C08F 220/34* | (2006.01) |

(52) U.S. Cl.
CPC .......... *A61K 9/5153* (2013.01); *A61K 9/5138* (2013.01); *A61K 31/05* (2013.01); *A61K 31/366* (2013.01); *A61L 29/085* (2013.01); *A61L 29/16* (2013.01); *A61M 25/10* (2013.01); *C08F 220/34* (2013.01); *A61L 2300/216* (2013.01); *A61L 2400/12* (2013.01); *A61M 2025/105* (2013.01)

(58) Field of Classification Search
CPC .... A61K 31/05; A61K 31/366; A61K 9/5138; A61K 9/5153; A61L 2300/216; A61L 2400/12; A61L 29/085; A61L 29/16; A61L 2300/416; A61L 2300/608; A61L 2300/624; A61L 29/06; A61M 2025/105; A61M 25/10; A61P 9/00; B01D 2239/10; B01D 39/14; C08F 220/34; C08F 220/14; C08F 220/1802; A61F 2/958; C08L 33/12; C08L 67/04; C08L 77/12

See application file for complete search history.

(56) References Cited

U.S. PATENT DOCUMENTS

| | | | |
|---|---|---|---|
| 6,022,901 A | 2/2000 | Goodman | |
| 6,663,881 B2 | 12/2003 | Kunz | |
| 8,992,471 B2* | 3/2015 | Dugas | A61P 9/00 |
| | | | 623/1.42 |
| 8,992,603 B2* | 3/2015 | Dugas | A61L 31/16 |
| | | | 604/890.1 |
| 2010/0331965 A1* | 12/2010 | Dugas | A61L 31/16 |
| | | | 623/1.42 |
| 2013/0096272 A1 | 4/2013 | Meier | |

(Continued)

FOREIGN PATENT DOCUMENTS

| | | |
|---|---|---|
| RU | 2373926 C1 | 11/2009 |
| WO | 99/13924 A2 | 3/1999 |
| WO | 2009061787 A1 | 5/2009 |

OTHER PUBLICATIONS

Conte et al.; "Recent Advances in Nanoparticle-Mediated Delivery of Anti-Inflammatory Phytocompounds"; Int. J. Mol. Sci.; 2017, 18, 709; published Mar. 28, 2017.*
English translation of: Krolevets Aleksandr Aleksandrovich et al, Compositions Containing Resveratrol Particles; and Method for Making Thereof (Versions), (Nov. 27, 2009).
US Department of Health and Human Services. National Institutes of Health. National Heart, Lung and Blood Institute. Facts about peripheral artery disease (P.A.D). 2006.
Fowkes FG, Rudan D, Rudan I, Aboyans V, Denenberg JO, McDermott MM, Norman PE, Sampson UK, Williams LJ, Mensah GA, Criqui MH. Comparison of global estimates of prevalence and risk factors for peripheral artery disease in 2000 and 2010: a systematic review and analysis. Lancet. 2013; 382(9901):1329-40.

(Continued)

*Primary Examiner* — Jeffrey T. Palenik
(74) *Attorney, Agent, or Firm* — Thomas| Horstemeyer, LLP

(57) ABSTRACT

In one aspect, the disclosure relates to compositions, methods, and devices pertaining to polymeric nanoparticle compositions (pNP), pNP compositions comprising a therapeutic agent, devices comprising a drug-coated balloon comprising a disclosed pNP comprising a therapeutic agent, and methods for treating peripheral artery disease using the disclosed compositions and devices. In further aspects, the pNP comprises a poly (lactic-co-glycolic) acid possessing a positive charge for firm attachment to the balloon matrix, followed by adhesion to the negatively charged bilayer of the vascular wall. In still further aspects, the therapeutic agent comprises a resveratrol or derivative thereof, a quercetin or derivative thereof, or combinations thereof. This abstract is intended as a scanning tool for purposes of searching in the particular art and is not intended to be limiting of the present disclosure.

18 Claims, 4 Drawing Sheets

(56) References Cited

U.S. PATENT DOCUMENTS

2015/0086613 A1   3/2015   DeRosa et al.

OTHER PUBLICATIONS

Bonaca MP, Scirica BM, Creager MA, Olin J, Bounameaux H, Dellborg M, Lamp JM, Murphy SA, Braunwald E, Morrow DA. Vorapaxar in patients with peripheral artery disease: results from TRA2{degrees}P-TIMI 50. Circulation. 2013; 127(14):1522-9, 1529e1-6.

Thukkani AK, Kinlay S. Endovascular intervention for peripheral artery disease. Circ Res. 2015; 116(9):1599-613.

De Labriolle A, Pakala R, Bonello L, Lemesle G, Scheinowitz M, Waksman R. Paclitaxel-eluting balloon: from bench to bed. Catheter Cardiovasc Interventions 2009; 73(5):643-52.

Byrne RA, Joner M, Alfonso F, Kastrati A. Drug-coated balloon therapy in coronary and peripheral artery disease. Nat Rev Cardiol. 2014; 11(1):13-23.

Nakazawa G, Finn AV, John MC, Kolodgie FD, Virmani R. The significance of preclinical evaluation of sirolimus-, paclitaxel-, and zotarolimus-eluting stents. Am J Cardiol. 2007; 100(8B):36M-44M.

Kleinedler JJ, Foley JD, Orchard E, Dugas, TR. Novel nanocomposite stent coating releasing resveratrol and quercetin reduces neointimal hyperplasia and promotes re-endothelialization. J. Control Rel. 2012; 159:27-33.

Kleinedler JJ, Pjescic I, Bullock KK, Khaliq A, Foley JD, Dugas TR. 2012. Arterial pharmacokinetics of red wine polyphenols: implications for novel endovascular therapies targeting restenosis. J Pharm Sci. 2012; 101(5):1917-31.

Yurdagul A Jr, Kleinedler JJ, McInnis MC, Khandelwal AR, Spence AL, Orr AW, Dugas TR. Resveratrol promotes endothelial cell wound healing under laminar shear stress through an estrogen receptor-$\alpha$-dependent pathway. Am J Physiol Heart Circ Physiol. 2014; 306(6):H797-806.

Astete CE, Sabliov CM. Synthesis and characterization of PLGA nanoparticles. J Biomater Sci Polym Ed. 2006;17(3):247-89.

Kleinedler JJ, Foley JD, Alexander JS, Roerig SC, Hebert VY, Dugas TR. Synergistic effect of resveratrol and quercetin released from drug-eluting polymer coatings for endovascular devices. J Biomed Mater Res B Appl Biomater. 2011; 99(2):266-75.

Kim D, El-Shall H, Dennis D, Morey T. Interaction of PLGA nanoparticles with human blood constituents. Colloids Surf B Biointerfaces. 2005. 40(2):83-91.

Davis BH, Jungerius B; International Council for the Standardization of Haematology (ICSH). International Council for Standardization in Haematology technical report Jan. 2009: new reference material for haemiglobincyanide for use in standardization of blood haemoglobin measurements. Int J Lab Hematol. 2010. 32(2):139-41.

Panyam J, Labhasetwar V. Dynamics of endocytosis and exocytosis of poly(D,L-lactide-co-glycolide) nanoparticles in vascular smooth muscle cells. Pharm Res. 2003. 20(2):212-20.

Finn AV, Nakazawa G, Joner M, Kolodgie FD, Mont EK, Gold HK, Virmani R. Vascular responses to drug eluting stents: importance of delayed healing. Arterioscler Thromb Vasc Biol. 2007. 27(7):1500-10.

Hsieh, Tze-Chen, et al., "Regulation of p53 and cell proliferation by resveratrol and its derivatives in breast cancer cells: an in silico and biochemical approach targeting integrin $\alpha v \beta 3$," International Journal of Cancer, 2011, pp. 2732-2743, vol. 129, doi: 10.1002/ijc.25930.

International Search Report for International Application No. PCT/US2019/16302, dated Mar. 27, 2019.

* cited by examiner

METHODS AND DEVICES FOR REDUCING VASCULAR SMOOTH MUSCLE CELL PROLIFERATION

CROSS-REFERENCE TO RELATED APPLICATIONS

This application is the 35 U.S.C. § 371 national stage of PCT application having serial number PCT/US2019/016302, filed on Feb. 1, 2019. This application also claims the benefit of and priority to U.S. Provisional Application Ser. No. 62/625,026, having the title "METHODS AND DEVICES FOR REDUCING VASCULAR SMOOTH MUSCLE CELL PROLIFERATION", filed on Feb. 1, 2018, the disclosure of which is incorporated herein by reference in its entirety.

BACKGROUND

Cardiovascular diseases (CVD) such as atherosclerosis result in a narrowing of arteries due to the formation of cholesterol-laden plaques within the vascular wall. These lesions eventually block blood flow to tissues. One such CVD is peripheral artery disease (PAD), which is characterized by a narrowing of arteries that supply blood to the extremities, particularly the legs. About 200 million people suffer from PAD worldwide (Fowkes, F. G., et al., Lancet. 2013; 382(9901):1329-40). PAD is defined by an arterial occlusion in the extremities, leading to pain, poor wound healing, and without intervention, limb loss and sometimes death. PAD is often associated with life-threatening conditions and events. For example, a recent study suggested that 11-12% of patients with stable but symptomatic PAD suffered death, myocardial infarction or stroke over a 36 month follow-up (Bonaca, M. P., et al., Circulation. 2013; 127(14): 1522-9)

Clinicians routinely correct arterial blockages by the inflation of a balloon within the affected area, a procedure known as angioplasty. Angioplasty is often accompanied by the placement of a stent, a metal tubular device meant to maintain blood flow long-term. However, unlike for coronary artery disease, in PAD, balloon angioplasty is the first line of therapy over stenting, since peripheral arteries are typically of small diameter, limiting the utility of stents (Thukkani A. K. and Kinlay S. Circ Res. 2015; 116(9):1599-613). Moreover, stents are associated with inflammation, late-term thrombosis, and stent fracture (ibid.). A complication of all forms of angioplasty is overstretch of the vessel occurring during balloon inflation often imparts strain to the vascular wall. This injury induces a series of cellular events culminating in the formation of a new lesion and eventually, a re-narrowing or "restenosis" of the lumen. These events include the loss of a functional endothelium, the adhesion of platelets and inflammatory cells in areas lacking an endothelium, and finally, the proliferation of vascular smooth muscle cells (VSMC). The latter event culminates in a vastly thickened vessel wall to impede blood flow.

Drug eluting stents releasing anti-mitogenic agents like paclitaxel or derivatives of sirolimus were developed to limit restenosis after coronary interventions, but their utility remains limited in small vessels (ibid.). Drug coated balloon (DCB) catheters comprising a shaft, extending from a tip (distal) to a connector (proximal), and a balloon which is expandable and which is covered or soaked with drug, in order to elute its drug directly on the target lesion. DCB catheters releasing paclitaxel have now been approved for use, but concerns are that the rapid release of paclitaxel will result in systemic toxicity, particularly given that current products release a significant amount of their paclitaxel loading prior to arrival at the lesion site (De Labriolle A, et al. Catheter Cardiovasc Interv. 2009; 73(5):643-52; Byrne, R. A., et al., Nat Rev Cardiol. 2014; 11(1):13-23). This is because these products use direct application of drug to the balloon surface, along with hydrophilic excipients like iopromide to facilitate tissue absorption (De Labriolle, A., op. cit.), but do little to prevent drug loss. Moreover, although paclitaxel reduces VSMC proliferation, it also impairs re-endothelialization and thus, dual antiplatelet therapies must be administered concurrently to prevent clotting (Nakazawa, G., et al., Am J Cardiol. 2007; 100(8B): 36M-44M). Unfortunately, these therapies increase the risk of bleeding, as well as costs associated with patient care.

Despite advances in research directed to improved methods and devices for drug eluting balloons, there remains a lack of drug eluting balloons that do not suffer from the negative side effects associated with paclitaxel and other anti-mitogenic agents. These needs and other needs are satisfied by the present disclosure.

SUMMARY

In accordance with the purpose(s) of the disclosure, as embodied and broadly described herein, the disclosure, in one aspect, relates to compositions, methods, and devices pertaining to polymeric nanoparticle compositions (pNP), pNP compositions comprising one or more therapeutic agent, devices comprising a drug-coated balloon comprising a disclosed pNP comprising the one or more therapeutic agent, and methods for treating peripheral artery disease using the disclosed compositions and devices. In further aspects, the pNP comprises a poly(lactic-co-glycolic) acid possessing a positive charge. In still further aspects, the one or more therapeutic agent comprises a resveratrol or derivative thereof, a quercetin or derivative thereof, or combinations thereof.

Disclosed are nanoparticle compositions comprising a first polymer, a second polymer, a first therapeutic agent, and optionally a second therapeutic agent; wherein the first polymer is an acrylate polymer comprising one or more positively charged moieties per polymer chain; wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone); wherein the first therapeutic agent is selected from the group consisting of resveratrol, pharmaceutically acceptable salts, and pharmaceutically acceptable derivatives thereof; and wherein the second therapeutic agent is quercetin, pharmaceutically acceptable salts, and pharmaceutically acceptable derivatives thereof.

Also disclosed are drug coated balloon catheters, comprising: an expandable balloon having an outer surface; and a nanoparticle coating the outer surface of the balloon catheter comprising a disclosed nanoparticle composition, wherein a concentration of the first active agent based on a surface area of the balloon ranges from about 1 to about 5 µg/mm², and a concentration of the second active agent based on the surface area of the balloon ranges from about 1 to about 5 µg/mm².

Also disclosed are methods for treating a vascular disease comprising treating a subject with a disclosed drug coated balloon catheter.

Also disclosed are kits comprising a disclosed drug coated balloon catheter and instructions for using the drug coated balloon catheter to treat a vascular disease.

Also disclosed are kits comprising a disclosed polymeric nanoparticle composition, instructions for coating the polymeric nanoparticle composition on an expandable balloon, and: (a) a balloon catheter comprising an expandable balloon; or (b) an expandable balloon suitable for use with a balloon catheter.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

Figure 1:
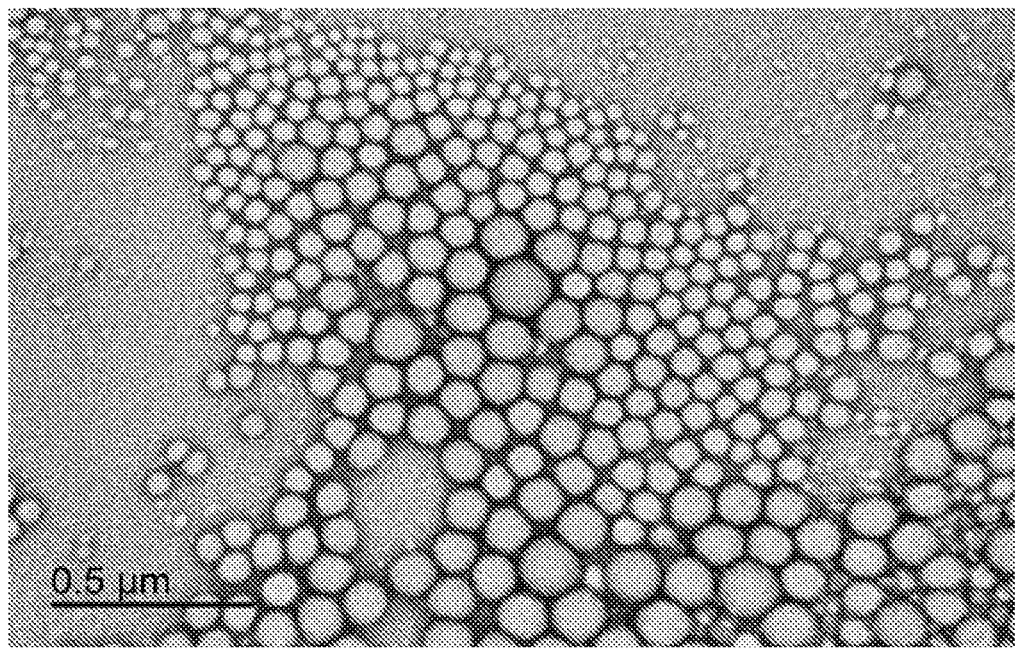
FIG. 1 shows a representative image of representative disclosed nanoparticles comprising poly(D,L-lactide-co-glycolide) and a cationic polymethacrylate. The image was obtained using transmission electron microscopy using methods described herein below.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein, in which some, but not all possible embodiments are shown. Indeed, disclosures may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Prior to describing the various embodiments, the following definitions are provided and should be used unless otherwise indicated.

A. DEFINITIONS

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, "comprising" is to be interpreted as specifying the presence of the stated features, integers, steps, or components as referred to, but does not preclude the presence or addition of one or more features, integers, steps, or components, or groups thereof. Additionally, the term "comprising" is intended to include examples encompassed by the terms "consisting essentially of" and "consisting of." Similarly, the term "consisting essentially of" is intended to include examples encompassed by the term "consisting of." As used herein, the terms "by", "comprising," "comprises", "comprised of," "including," "includes," "included," "involving," "involves," "involved," and "such as" are used in their open, non-limiting sense.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Reference to "a" chemical compound refers one or more molecules of the chemical compound, rather than being limited to a single molecule of the chemical compound. Furthermore, the one or more molecules may or may not be identical, so long as they fall under the category of the chemical compound. Thus, for example, "a" PLGA is interpreted to include one or more polymer molecules of the PLGA, where the polymer molecules may or may not be identical (e.g., different molecular weights and/or isomers).

It should be noted that ratios, concentrations, amounts, and other numerical data can be expressed herein in a range format. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'". It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.4%, 3.2%, and 4.4%) within the indicated range.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this invention belongs.

The term "alkyl group" as used herein is a branched or unbranched saturated hydrocarbon group of 1 to 24 carbon atoms, such as methyl, ethyl, n propyl, isopropyl, n butyl, isobutyl, t butyl, pentyl, hexyl, heptyl, octyl, decyl, tetra-decyl, hexadecyl, eicosyl, tetracosyl and the like. A "lower alkyl" group is an alkyl group containing from one to six carbon atoms.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

As used herein, the terms "number average molecular weight" or "$M_n$," can be used interchangeably, and refer to the statistical average molecular weight of all the polymer chains in the sample and is defined by the formula:

$$M_n = \frac{\sum N_i M_i}{\sum N_i},$$

where $M_i$ is the molecular weight of a chain and $N_i$ is the number of chains of that molecular weight. $M_n$ can be determined for polymers, e.g., polycarbonate polymers, by methods well known to a person having ordinary skill in the art using molecular weight standards, e.g. polycarbonate standards or polystyrene standards, preferably certified or traceable molecular weight standards.

As used herein, a "polymer" refers to a molecule comprised of repeating "constitutional units." The constitutional units derive from the reaction of monomers. The constitutional units themselves can be the product of the reactions of other compounds. A polymer may be derived from the polymerization of two or more different monomers and therefore may comprise two or more different constitutional units. Such polymers are referred to as "copolymers." "Terpolymers" are a subset of "copolymers" in which there are three different constitutional units. Those skilled in the art, given a particular polymer, will readily recognize the constitutional units of that polymer and will readily recognize the structure of the monomer from which the constitutional units derive. Polymers may be straight chain, branched chain, star-like or dendritic. One polymer may be attached (grafted) onto another polymer. The constitutional units of polymers may be randomly disposed along the polymer chain, may be present as discrete blocks, may be so disposed as to form gradients of concentration along the polymer chain, or a combination thereof. Polymers may be cross-linked to form a network.

As used herein, the term "units" can be used to refer to individual (co)monomer units such that, for example, glycolide repeat units refers to individual styrene (co)monomer units in the polymer. In addition, the term "units" can be used to refer to polymeric block units such that, for example, "glycolide repeating units" can also refer to glycolid blocks; "units of polylactide" refers to block units of polylactide; "units of polyglycolide" refers to block units of polyglycolide; and so on. Such use will be clear from the context.

The term "copolymer" refers to a polymer having two or more monomer species, and includes terpolymers (i.e., copolymers having three monomer species).

As used herein, "incorporated into" or "encapsulated by" a nanoparticle or pNP refers to a therapeutic agent that is physically entrapped within the matrix formed by the polymer forming the nanoparticle.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

The term "contacting" as used herein refers to bringing a disclosed compound and a cell, a target protein, or other biological entity together in such a manner that the compound can affect the activity of the target, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "therapeutic agent" also refers to pharmaceutically acceptable, pharmacologically active derivatives of those therapeutic agent disclosed herein, such as resveratrol and quercetin, including, but not limited to, salts, esters, amides, hydrates, solvates, and the like.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, a "cardiovascular disease" is a disease, condition, or disorder that impacts the heart, circulatory system, or both the heart and the circulatory system. The circulatory system includes the cardiovascular system, and the lymphatic system. The lymphatic system distributes lymph. The cardiovascular system is a system of blood vessels, primarily arteries and veins, which transport blood to and from the heart, brain and peripheral organs such as, without limitation, the arms, legs, kidneys and liver. The coronary artery system supplies blood to the heart. The carotid artery system supplies blood to the brain. The peripheral vascular system carries blood to (via arteries) and from (via veins) the peripheral organs such as, without limitation, the hands, legs, kidneys and liver. The coronary artery system, carotid artery system, and the peripheral vascular system which includes the peripheral artery system are sub-systems of the cardiovascular system.

As used herein, a "vascular disease" generally refers to a disease, condition, or disorder that impacts the circulatory system. In particular "vascular disease" includes a disease, disorder, or condition of the coronary system, the carotid system and the peripheral vascular system.

"Vascular diseases" are a subset of "cardiovascular diseases."

Examples of cardiovascular diseases include diseases of the heart which include, but are not limited to, heart valve disease, arrhythmia, heart failure, and congenital heart disease, and vascular diseases which include, but are not limited to atherosclerosis, thrombosis, restenosis, hemorrhage, vascular dissection or perforation, vulnerable plaque, chronic total occlusion, claudication, anastomotic proliferation for vein and artificial grafts, peripheral artery disease, carotid artery disease, coronary artery disease, aneurysm, renal (kidney) artery disease, Raynaud's syndrome, Buerger's disease, peripheral venous disease, varicose veins, blood clots in the veins, blood clotting disorders, and lymphdema.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, vascular grafts, self-expandable stents, balloon-expandable stents, and stent-grafts.

One type of implantable medical device is a stent. Stents are implantable medical devices that are generally cylindrically shaped, and function to hold open, and sometimes expand, a segment of a blood vessel or other lumen or vessel in a patient's body when the vessel is narrowed or closed due to diseases or disorders including, without limitation, coronary artery disease, carotid artery disease and peripheral arterial disease. A stent can be used in, without limitation, neuro, carotid, coronary, pulmonary, renal, biliary, iliac, femoral and popliteal, as well as other peripheral vasculatures, as well as other bodily lumens. A stent can be used in the treatment or prevention of vascular disorders, as well as other disorders. For a stent, the "outer surface" includes the luminal surface which faces the lumen interior, the abluminal surface which faces the lumen wall, and sidewall surfaces, if present, which connect the abluminal and luminal surfaces.

A "catheter" is a thin, flexible tube for insertion into a natural body cavity, duct, or vessel, and may be used to introduce or remove fluid, to distend the vessel, or to hold open the vessel or cavity.

A "vascular catheter" is an example of an insertable medical device. A vascular catheter is a thin, flexible tube with a manipulating means at one end, which remains outside the patient's body, and an operative device at or near the other end, which is inserted into the patient's artery or vein. The catheter may be used for the introduction of fluids, often containing drugs, to the target site. The catheter may be used to deliver a stent to the target site, or may be used to deliver a balloon used in angioplasty. The catheter may perform multiple functions.

As used herein, a "balloon" comprises a relatively thin, flexible material, forming a tubular membrane, and is usually associated with a vascular catheter. When positioned at a particular location in a patient's vessel can be expanded or inflated to an outside diameter that is essentially the same as the inside or luminal diameter of the vessel in which it is placed. Balloons may be inflated, without limitation, using a liquid medium such as water or normal saline solution (where saline means including salt, typically sodium chloride), that is, saline that is essentially isotonic with blood.

A "balloon catheter" refers to a medical device which is a system of a catheter with a balloon at the end of the catheter.

With respect to a DCB catheter balloon, the "outer surface" is meant any surface however spatially oriented that is in contact with a bodily tissue, such as a vessel wall, or fluid.

Unless otherwise specified, temperatures referred to herein are based on atmospheric pressure (i.e. one atmosphere).

Certain abbreviations used herein are defined as follows:
d is day or days;
DCB is drug coated balloon;
min is minute or minutes;
pNP is a disclosed polymeric nanoparticle as disclosed herein throughout, optionally comprising a therapeutic agent such as a polyphenol composition comprising TAR and QUER
QUER is quercetin; and
RESV is resveratrol;
s and sec can be used interchangeable and refer to second or seconds; and
TAR is triacetyl resveratrol.

B. POLYMERIC NANOPARTICLE (PNP) COMPOSITIONS

The delivery of bioactives to vascular cells requires a system that can target the vascular tissue and release a therapeutic agent for clinical effect. Currently available DCB catheter balloons use only hydrophilic excipients such as urea, citrate or iopromide for facilitating transfer within the tissue but do little to facilitate adhesion and maximal transfer. To achieve adequate deposition and delivery of bioactives, disclosed herein are novel polymeric nanoparticle (pNP) compositions comprising one or more therapeutic agent comprise two novel components: (1) one or more anti-proliferative therapeutic agents that inhibit restenosis of the vessel and also facilitate re-endothelization of the vessel wall, e.g., resveratrol or derivative thereof and/or quercetin or derivative thereof, entrapped or encapsulated within a hydrophobic polymeric nanoparticle matrix, and (2) a nanoparticle comprising a polymer with a cationic moieties at physiological pH. Without wishing to be bound by a particle theory, the polymer with cationic moieties is believed to form, at least in part, an outer cationic layer. If the cationic moieties comprise a permanent charge, e.g., a quanternary ammonium moiety, then the outer cationic layer is charged regardless of local pH. Thus, disclosed pNPs encapsulating a resveratrol and a quercetin (e.g., triacetyl resveratrol and quercetine entrapped pNPs) can be released after inflation of the balloon, promoting attachment to the vasculature upon its contact with the balloon surface.

In one aspect, the disclosure relates to polymeric nanoparticle compositions (pNP) and pNP compositions comprising one or more therapeutic agent. The disclosed pNP compositions comprising one or more therapeutic agent can be used with devices comprising a drug-coated balloon comprising, as well as used in methods for treating peripheral artery disease using the disclosed compositions and devices. In further aspects, the pNP comprises at least one polymer possessing a positive charge, e.g., as provided by a quanternary ammonium moiety. Without wishing to be bound by a particular theory, a pNP comprising a polymer possessing a positive charge allows for firm attachment to the balloon matrix, followed by adhesion to the negatively charged bilayer of the vascular wall. In yet further aspects, the at least one polymer possessing a positive charge is a poly(lactic-co-glycolic) acid possessing a positive charge. In still further aspects, the pNP comprises one or more therapeutic agent comprising a resveratrol or derivative thereof, a quercetin or derivative thereof, or combinations thereof.

In one aspect, the disclosure relates to pNP encapsulating one or more therapeutic agents. In a further aspect, a pNP encapsulates a therapeutic agent selected from the group consisting of resveratrol, pharmaceutically acceptable salts, and pharmaceutically acceptable derivatives thereof. In a further aspect, a pNP encapsulates a therapeutic agent selected from the group consisting of quercetin, pharmaceutically acceptable salts, and pharmaceutically acceptable derivatives thereof. In a still further aspect, a pNP encapsulates a first therapeutic agent selected from the group consisting of resveratrol, pharmaceutically acceptable salts, and pharmaceutically acceptable derivatives thereof, and an optional second therapeutic agent selected from the group consisting of quercetin, pharmaceutically acceptable salts, and pharmaceutically acceptable derivatives thereof.

In various aspects, the ratio of therapeutic agents is in the range selected from the group consisting of about 1:5, about 1:2, and about 1:1 resveratrol to quercetin by weight percent. The disclosure further provides a pNP comprising a first active agent and second active agent in a ratio which is selected from the group consisting of about 1:1, about 1:2, about 2:1, about 1:2.5, about 2.5:1, about 1:4, about 4:1, about 1:5, about 5:1, about 1:10, about 10:1, about 1:20, about 20:1, about 1:25, about 25:1, about 1:50, about 50:1, about 1:100, about 100:1, about 1:200, about 200:1, about 1:250, about 250:1, about 1:500, and about 500:1 by weight percent.

In various aspects, a pNP comprises a first polymer possessing at least one positive charge per polymer chain and a second polymer.

In a further aspect, the first polymer is an acrylate polymer comprising one or more positively charged moieties per polymer chain. In various aspects, a "positively charged moiety" comprises a functional group that can be positively charged at physiological pH or carries a positive charge via a covalent structure such as a quaternary ammonium groups. In a further aspect, a moiety with a positive charge is an ammonium moiety, a quaternary ammonium moiety, or combinations thereof. In a further aspect, the first polymer is an acrylate polymer comprising one or more positively charged moieties per polymer chain. In a still further aspect, the acrylate polymer is a methacrylate polymer. In a still further aspect, the first polymer is a copolymer of acrylic acid and methacrylic acid having a low proportion of quaternized ammonium groups. In a yet further aspect, the first polymer is a copolymer or of a mixture of copolymers composed of 85 to 98% by weight free-radical polymerized C1- to C4-alkyl esters of acrylic or methacrylic acid and 15 to 2% by weight (meth)acrylate monomers with a quaternary ammonium group in the alkyl radical. In a still further aspect, the first polymer is a (meth)acrylate copolymers comprising monomers with quaternary ammonium groups, e.g. trimethylammoniumethyl methacrylate chloride, such as those described in EP-A-181 515 and DE 1 617 751. In an even further aspect, the first polymer is a quaternized dimethylaminoethyl methacrylate copolymer.

In a further aspect, the first polymer comprises C1- to C4-alkyl esters of acrylic or methacrylic acid are methyl acrylate, ethyl acrylate, butyl acrylate, butyl methacrylate and methyl methacrylate. In a still further aspect, the first polymer comprises (meth)acrylate monomer with quaternary ammonium groups is 2-trimethylammoniumethyl methacrylate chloride.

In a further aspect, the first polymer comprises a copolymer produced, for example, from 93 to 98% by weight free-radical polymerized C1- to C4-alkyl esters of acrylic or methacrylic acid and 7-2% by weight 2-trimethylammoniumethyl methacrylate chloride. In a still further aspect, such a polymer comprises 50-70% by weight methyl methacrylate, 20-40% by weight ethyl acrylate. In a yet further aspect, the first polymer comprises a copolymer composed, for example, of 65% by weight methyl methacrylate, 30% by weight ethyl acrylate and 5% by weight 2-trimethylammoniumethyl methacrylate chloride. An appropriate polymer is this type is available under the tradename EUDRAGIT® RS ammonio methacrylate copolymer available from Evonik.

In a further aspect, the first polymer comprises a copolymer produced, for example, from 85 to less than 93% by weight free-radical polymerized C1- to C4-alkyl esters of acrylic or methacrylic acid and 15 to more than 7% by weight 2-trimethylammoniumethyl methacrylate chloride. In a still further aspect, such a polymer comprises 50-70% by weight methyl methacrylate, 20-40% by weight ethyl acrylate. In a yet further aspect, the first polymer comprises a copolymer composed, for example, 60% by weight methyl methacrylate, 30% by weight ethyl acrylate and 10% by weight 2-trimethylammoniumethyl methacrylate chloride. An appropriate polymer is this type is available under the tradename EUDRAGIT® RL ammonio methacrylate copolymer available from Evonik.

The first polymer can be prepared by bulk polymerization in the presence of a free-radical initiator dissolved in a monomer mixture. The polymer can likewise also be produced by a solution or precipitation polymerization. The polymer can be obtained in this way in the form of a fine powder, which is achievable in the case of bulk polymerization by grinding, and in the case of solution and precipitation polymerization for example by spray drying.

In various aspects, the second polymer is selected from the group consisting of poly(lactide), poly(glycolide), poly(lactide-co-glycolide), poly(caprolactone), poly(lactide-co-caprolactone), poly(glycolide-co-caprolactone), and poly(D,L-lactide-co-glycolide-co-ε-caprolactone). In a still further aspect, the second polymer is an A-B block copolymers, wherein block A can be a poly(lactide), a poly(glycolide), or a poly(caprolactone), and wherein block B be independently a polymer distinct from block A and selected from a poly(lactide), a poly(glycolide), or a poly(caprolactone). In a yet further aspect, the second polymer is a terpolymer. The terpolymer may be an alternating, random alternating or purely random copolymer or a block copolymer.

In a further aspect, the second polymer is a copolymer of lactide and glycolide, i.e., a poly(lactide-co-glycolide), abbreviated as PLGA. In a still further aspect, the second polymer is a PLGA with a molar ratio of lactide to glycolide in the PLGA can be 90:10 to 10:90. In a yet further aspect, the second polymer is a PLGA with a molar ratio of lactide to glycolide of 75:25 to 25:75. In an even further aspect, the second polymer is a PLGA with a molar ratio of lactide to glycolide of 60:40 to 40:60. In some aspects, the second polymer is a PLGA with a molar ratio of lactide to glycolide of 50:50. An exemplary PLGA is commercially available under the tradename of Resomer® PLGA such as Resomer® RG504H poly(lactic-co-glycolic acid) PLGA 50:50.

In a further aspect, the second polymer is a PLGA with a molecular weight of about 5,000 to about 100,000 Dalton. In a still further aspect, the second polymer is a PLGA with a molecular weight of about 30,000 to about 60,000 Dalton. In an even further aspect, the second polymer is a PLGA with a molecular weight of about 35,000 to about 57,000 Dalton. In a still further aspect, the second polymer is a PLGA with a molecular weight of about 38,000 to about 54,000 Dalton. As used herein, the term "molecular weight" refers to "weight average molecular weight."

The disclosed pNP can be formed by various techniques suitable for forming nanoparticles comprising the disclosed first polymer and second polymer, e.g., a single emulsion evaporation technique. Briefly, an organic phase is created by mixing the first polymer and the second polymer in the presence of suitable organic solvents. The weight ratio of first polymer to second polymer can be about 1:1 to about 1:10. In a further aspect, the weight ratio of first polymer to second polymer is about 1:2 to about 1:4. Suitable solvents include ethyl acetate to acetone in a volume ratio of about 8:2. Once stirred, the first therapeutic agent and optional second therapeutic agent are added to the organic phase prepared as described above. Formation of nanoparticles encapsulating one or more therapeutic agent can then accomplished by adding the foregoing in dropwise to an aqueous phase that can optionally comprise a detergent such as Tween 80. The preparation can further comprise microfluidizing the emulsion thus formed. The emulsion or microfluidize emulsion can then have the organic phase removed under reduced pressure evaporation (e.g., "rotovapped"), followed by mixing the resulting nanoparticle suspension with an agent such as trehalose in a suitable amount, e.g., a 1:2 mass ratio of nanoparticle suspension to trehalose. The mixture can further comprise a suitable aggregation disrupting agent, e.g., polyvinyl alcohol, added at a mass ratio of aggregation disrupting agent to nanoparticle suspension of about 1:4 to about 1:10.

In various aspects, a weight ratio of first polymer to second polymer can be about 1:1, 1:2, 1:3, 1:4, 1:5, 1:6, 1:7, 1:8, 1:9, 1:10; any combination of the foregoing ratios, or any range encompassed by any two of the foregoing ratios. In a further aspect, a weight ratio of first polymer to second polymer can be about 1.0:1.0, 1.0:1.1, 1.0:1.2, 1.0:1.3, 1.0:1.4, 1.0:1.5, 1.0:1.6, 1.0:1.7, 1.0:1.8, 1.0:1.9, 1.0:2.0, 1.0:2.1, 1.0:2.2, 1.0:2.3, 1.0:2.4, 1.0:2.5, 1.0:2.6, 1.0:2.7, 1.0:2.8, 1.0:2.9, 1.0:3.0, 1.0:3.1, 1.0:3.2, 1.0:3.3, 1.0:3.4, 1.0:3.5, 1.0:3.6, 1.0:3.7, 1.0:3.8, 1.0:3.9, 1.0:4.0, 1.0:4.1, 1.0:4.2, 1.0:4.3, 1.0:4.4, 1.0:4.5, 1.0:4.6, 1.0:4.7, 1.0:4.8, 1.0:4.9, 1.0:5.0, 1.0:5.1, 1.0:5.2, 1.0:5.3, 1.0:5.4, 1.0:5.5, 1.0:5.6, 1.0:5.7, 1.0:5.8, 1.0:5.9, 1.0:6.0, 1.0:6.1, 1.0:6.2, 1.0:6.3, 1.0:6.4, 1.0:6.5, 1.0:6.6, 1.0:6.7, 1.0:6.8, 1.0:6.9, 1.0:7.0, 1.0:7.1, 1.0:7.2, 1.0:7.3, 1.0:7.4, 1.0:7.5, 1.0:7.6, 1.0:7.7, 1.0:7.8, 1.0:7.9, 1.0:8.0, 1.0:8.1, 1.0:8.2, 1.0:8.3, 1.0:8.4, 1.0:8.5, 1.0:8.6, 1.0:8.7, 1.0:8.8, 1.0:8.9, 1.0:9.0, 1.0:9.1, 1.0:9.2, 1.0:9.3, 1.0:9.4, 1.0:9.5, 1.0:9.6, 1.0:9.7, 1.0:9.8, 1.0:9.9, 1.0:10.0; any combination of the foregoing ratios, or any range encompassed by any two of the foregoing ratios.

In various aspects, the disclosed nanoparticles are about 50 nm to about 500 nanometers in diameter. In a further aspect, the disclosed nanoparticles are about 100 nm to about 500 nanometers in diameter, about 100 nm to about 400 nanometers in diameter, about 100 nm to about 300 nanometers in diameter, or about 100 nm to about 200 nanometers in diameter. In a still further aspect, the disclosed nanoparticles are about 150 nm to about 500 nanometers in diameter, about 150 nm to about 400 nanometers in diameter, about 150 nm to about 300 nanometers in diameter, or about 150 nm to about 200 nanometers in diameter. In a yet further aspect, the disclosed nanoparticles have a diameter of about 50 nm, 100 nm, 120 nm, 130 nm, 150 nm, 160 nm, 170 nm, 180 nm, 190 nm, 200 nm, 210 nm, 220 nm, 230 nm, 240 nm, 250 nm, any combination of the foregoing values, or any range encompassed by the foregoing values.

In various aspects, the disclosed nanoparticles have a polydisperse index of about 0.05 to about 0.25. In a further aspect, the disclosed nanoparticles have a polydisperse index less than about 0.10, 0.11, 0.12, 0.13, 0.14, 0.15, 0.16, 0.17, 0.18, 0.19, 0.20, 0.21, 0.22, 0.23, 0.24, or 0.25. In a still further aspect, the disclosed nanoparticles have a polydisperse index of about 0.10, 0.11, 0.12, 0.13, 0.14, 0.15, 0.16, 0.17, 0.18, 0.19, 0.20, 0.21, 0.22, 0.23, 0.24, 0.25, any combination of the foregoing values, or any range encompassed by the foregoing values.

In various aspects, the disclosed nanoparticles have a positive zeta potential at physiological pH. In a further aspect, the disclosed nanoparticles have a zeta potential (expressed in mV) at physiological pH of about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, any combination of the foregoing values, or any range encompassed by the foregoing values.

Invarious aspects, the disclosed nanoparticles have a pH-independent positive zeta potential. In a further aspect, the disclosed nanoparticles have a pH-independent zeta potential (expressed in mV of about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, any combination of the foregoing values, or any range encompassed by the foregoing values.

C. RESVERATROL

In various aspects, the present disclosure relates to the administration of resveratrol or derivatives thereof to a subject in order to prevent restenosis and/or the progression or recurrence of coronary heart disease.

Resveratrol may be administered in natural form, i.e., as isolated from grape skins, wine or other plant-derived compositions, or it may be administered as chemically synthesized in the laboratory (e.g., using the methods of Moreno-Manas et al., (1985) Anal. Quim 81:157-61; Jeandet et al., (1991) Am. J. Enol. Vitic. 42:41-46; or Goldberg et al. (1994) Anal. Chem. 66:3959-63), or as obtained commercially, e.g., from the Sigma-Aldrich Corporation (St. Louis, Mo.).

The resveratrol active agent may be administered in the form of a pharmacologically acceptable salt, ester, amide, prodrug or analog, or as a combination thereof. However, conversion of an inactive ester, amide, prodrug or analog to an active form must occur prior to or upon reaching the target tissue or cell. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature (see U.S. Pat. No. 6,022,901).

Resveratrol is known chemically as 3,4',5-Trihydroxy-trans-stilbene, 5-[(1E)-2-(4-Hydroxyphenyl)ethenyl]-1,3-benzenediol. It has the structure given in Formula I.

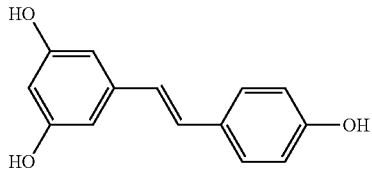

Formula I

Non-limiting examples of derivatives of cis- and trans-resveratrol are those in which the hydrogen of one or more of the compounds' hydroxyl groups is replaced to form esters or ethers (for example, see Formula I). Ether formation examples include, but are not limited to, the addition of alkyl chains such as methyl and ethyl groups, as well as conjugated mono- or disaccharides such as glucose, galactose, maltose, lactose and sucrose. Additional modifications at the hydroxyl groups might include glucuronidation or sulfation.

Non-limiting examples of derivatives of cis- and trans-resveratrol are those in which the hydrogen of one or more of the compounds' hydroxyl groups is replaced to form esters or ethers (for example, see Formula I). Ether formation examples include, but are not limited to, the addition of alkyl chains such as methyl and ethyl groups, as well as conjugated mono- or disaccharides such as glucose, galactose, maltose, lactose and sucrose. Additional modifications at the hydroxyl groups might include glucuronidation or sulfation.

Esterification products include, but are not limited to, compounds formed through the addition of amino acid segments such as RGD or KGD or other compounds resulting from the reaction of the resveratrol hydroxyl groups with other carboxylic acids.

Additional derivatives include, but are not limited to, those compounds that result from the oxidative dimerization of or functional group addition to the parent resveratrol compound or to a functionalized resveratrol variant. Examples of these compounds include materials resulting from the addition of hydroxyl, methoxy and ethoxy groups at the 4, 2', and 3' positions. Dimerization results from the reaction of the ethane bond of one resveratrol molecule with one of the hydroxyl groups on a second resveratrol molecule resulting in the formation of a fused ring system. Alkylation at the 4, 2', and 3' positions creates other derivatives through the addition of groups including, but not limited to, methyl, ethyl, and propyl, as well as the addition of larger carbon chains such as 4-methyl-2-pentene, 4-methyl-3-pentene and isopentadiene.

Additional derivatives include, but are not limited to, compounds that arise from the loss of any of the hydroxyl groups of the parent molecule, addition of hydroxyl groups at alternate positions, and any compound that may arise from the previously mentioned reactions to provide a functionalized variant of the dehydroxylated compound.

Structures of exemplary resveratrol derivatives are shown below in Formulas II-VII. The structure of triacetyl resveratrol (TAR) is given in Formula VII.

Formula II
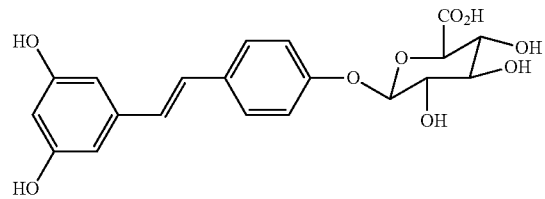

Formula III
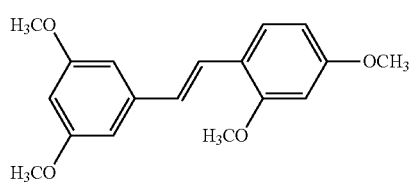

Formula IV
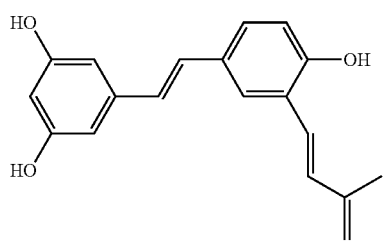

Formula V
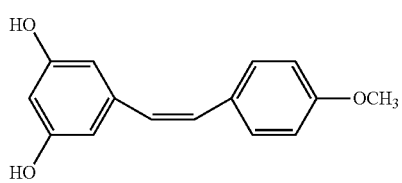

Formula VI
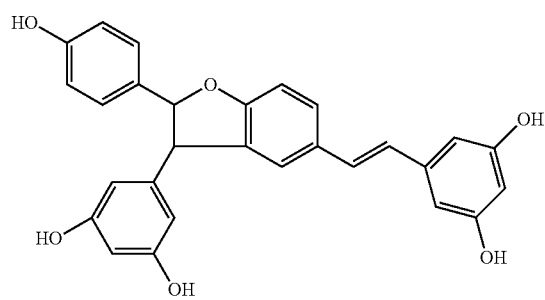

Formula VII
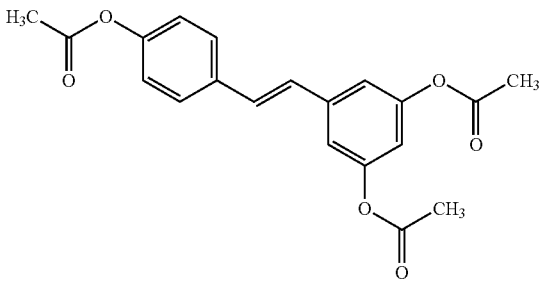

Resveratrol may be involved in many pathways of restenosis. Thus, as used in the disclosed compositions, devices, and methods, resveratrol may address many if not all targets causing a problem from restenosis. For instance, it provides anti-inflammatory benefits and promotes endothelial cell function. Reports have shown that resveratrol stimulates the growth of endothelial progenitor cells, both in vivo and in vitro (see J. Gu, et al., 2006, J Cardiovasc Pharmacol., 47(5): 711-721). Without wishing to be bound by a particular theory, it is possible that this may be a key step in re-endothelialization.

Resveratrol also increases endothelial nitric oxide synthase activity (see Wallerath T et al., Circulation. 2002 Sep. 24; 106(13):1652-8.) Further, resveratrol enhances endothelium-dependent vasorelaxation (Rush J W, Quadrilatero J, Levy A S, Ford R J. Exp Biol Med (Maywood). 2007 June; 232(6):814-22). Therefore, utilizing resveratrol in a DCB and/or other medical device according to the present disclosure provides a multi-faceted approach to reducing restenosis and improving blood flow after stent implantation.

For more information on the use of resveratrol in the treatment of restenosis through methods other than drug-eluting stents, see U.S. Pat. No. 6,022,901, to David William Goodman, titled "Administration of resveratrol to prevent or treat restenosis following coronary intervention", which is herein incorporated by reference in its entirety.

Resveratrol is a polyphenol that has been linked to the reported cardioprotection of red wine consumption. The reported cardioprotective effects of red wine consumption was prompted by epidemiological studies documenting the "French Paradox," a term coined to describe the reduced incidence of death due to CHD in areas of southwest France. Inhabitants of this area exhibit increased serum cholesterol and blood pressure and eat more lard and butter than do Americans, yet suffer 40% fewer deaths due to CHD than other western societies. This paradoxical effect is attributed to their daily consumption of red wine. While epidemiological studies suggest a decreased risk of CHD in populations regularly consuming alcohol, considerable data indicate that wine provides greater protection as compared to other alcoholic beverages.

Resveratrol is a phytoalexin polyphenol found in foods such as grapes, mulberries, peanuts, and grapevine. Within the grape itself, resveratrol is most abundant in the skin (ca. 50-100 μg/gm. One fluid ounce of red wine provides "160 μg resveratrol. The rapid conjugation of resveratrol to form glucuronides and sulfates has been argued as evidence that orally administered resveratrol concentrations cannot approach therapeutically useful levels. However, immediately after consumption, resveratrol can be measured in the plasma, heart, liver, and kidney. Chronic consumption further increases levels of resveratrol in tissues such as the heart and liver.

Prior reports by other laboratories have indicated that resveratrol acts through a variety of mechanisms to promote vascular health. As an antioxidant polyphenol, it limits the oxidation of low-density lipoprotein, thus inhibiting fatty streak formation. It furthermore exhibits anti-inflammatory effects through an inhibition of NFκB activation. Several labs have demonstrated that resveratrol promotes endothelial function by increasing eNOS activity, and a recent report suggests that the mechanism for this effect is an increase in eNOS phosphorylation. Resveratrol also promotes endothelial protection against oxidant injury, likely via an inhibition of the activation of NADPH oxidase. Finally, resveratrol inhibits adhesion of inflammatory cells to the vascular endothelium by inhibiting the expression of adhesion molecules.

Prior reports demonstrate resveratrol's efficacy in inhibiting proliferation of vascular smooth muscle cells (VSMC). For example, in VSMC stimulated with the mitogens endothelin-1 and platelet-derived growth factor, resveratrol inhibited cell cycle traverse, and in coronary artery smooth muscle, resveratrol inhibited endothelin-1-induced map kinase stimulation.

The mechanisms for these effects are due in part to a resveratrol-mediated ER activation that culminates in an upregulation of tetrahydrobiopterin (BH4) biosynthesis. The inventors have demonstrated that the resulting increase in levels of BH4, a known NOS cofactor, promoted an elevation in NO concentration that culminated in cell cycle arrest. Effects on NO concentration are dependent upon an increase in inducible nitric oxide synthase (iNOS) activity, but not its expression. In addition to this novel ER-dependent pathway, the current invention also shows that resveratrol inhibits NFκB activation very potently.

Thus, according to the present invention, resveratrol exerts pleiotropic effects on VSMC proliferation, enhancing NO production through an ER-dependent pathway, but also inhibits NFκB activation through an ER-independent pathway. It is the cooperativity between these two pathways that accounts for the observed effects on VSMC proliferation.

Resveratrol has same binding site as estradiol and behaves as an ER-alpha agonist, however, it has a lower binding affinity than estradiol. This provides protection against estrogenic side effects, such as alternation of the female menstrual cycle and feminization side-effects in males.

D. QUERCETIN

In various aspects, the present disclosure relates to the administration of quercetin or derivatives thereof to a subject in order to prevent restenosis and/or the progression or recurrence of coronary heart disease.

Quercetin is typically found in plants as glycone or carbohydrate conjugates. Quercetin itself is an aglycone or aglucon. That is, quercetin does not possess a carbohydrate moiety in its structure. Analogs of quercetin include its glycone conjugates include rutin and thujin. Rutin is also known as quercetin-3-rutinoside. Thujin is also known as quercitrin, quercetin-3-L-rhamnoside, and 3-rhamnosylquercetin. Onions contain conjugates of quercetin and the carbohydrate isorhamnetin, including quercetin-3,4'-di-O-beta glucoside, isorhamnetin-4'-O-beta-glucoside and quercetin-4'-O-beta-glucoside. Quercetin itself is practically insoluble in water. The quercetin carbohydrate conjugates have much greater water solubility then quercetin.

Quercetin is known chemically as 2-(3,4-dihydroxyphenyl)-3,5,7-trihydroxy-4H-1-benzopyran-4-one and 3,3',4'5,7-pentahydroxy flavone. It has the structure given in Formula VIII.

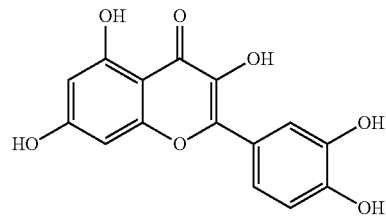

Formula VIII

Quercetin is a phenolic antioxidant and has been shown to inhibit lipid peroxidation. In vitro and animal studies have shown that quercetin inhibits degranulation of mast cells, basophils and neutrophils. Such activities account, in part, for quercetin's anti-inflammatory and immunomodulating activities. Other in vitro and animal studies show that quercetin inhibits tyrosine kinase and reduces the activation of the inflammatory mediator, NF-κB. Further activities of quercetin include anti-viral and anti-cancer activity. Quercetin is further known to inhibit aldose reductase. A quercetin or an analog thereof for use in the present invention can be an inhibitor of tyrosine kinases. The most important biologic activities of quercetin are its inhibition of platelet activation plus its anti-inflammatory properties, as the interaction of these two effects can reduce the incidence of thrombogenesis associated with current generation DES. Quercetin inhibits both platelet activation and platelet aggregation. It enhances platelet-derived nitric oxide to inhibit the activation of a protein kinase C-dependent NADPH oxidase. In addition, quercetin inhibits platelet aggregation through its inhibition of phosphoinositide kinase. Further properties of quercetin or its analogs that are relevant in the context of the present invention include: inhibition of cell cycle, inhibition of smooth muscle cell proliferation and/or migration. Suitable analogs/derivatives of quercetin include its glycone conjugates rutin and thujin (See U.S. Patent Application Publication No. 2007/0212386 (Patravale et al.)).

Quercetin and/or its analogs may be capable of exerting the above activities when used singly. However, the above properties of quercetin and/or its analogs may be further enhanced by exploiting the synergy between quercetin and/or its analogs and further therapeutic agents (as disclosed herein), such as resveratrol and/or its derivatives.

In one embodiment, the combination of polymer and pharmaceutically active agent comprise a combination of pharmaceutically active agents. If more than one pharmaceutically active agent is used, they can be present in combination in the same layer, or in separate polymer layers. Exemplary combinations include resveratrol plus quercetin separately or in combination in one or more coatings and resveratrol or quercetin alone or in combination in one or more coatings.

Exemplary derivatives of quercetin are those in which the hydrogen of one or more of the compounds' hydroxyl groups, most commonly the 3 hydroxyl is replaced to form esters or ethers (see for example Formula VIII). Ether formation examples include, but are not limited to, the addition of alkyl chains such as methyl and ethyl groups, as well as deoxy sugars such as fucose and rhamnose. Esterification products include, but are not limited to; compounds formed through the reaction of carboxylic acid containing materials such as acetic acid, propionic acid and palmitic acid. Urethane derivatives of quercetin include, but are not limited to; amino acid ester carbamates formed by the addition of materials such as benzyl 2-isocyanatoacetate and (S)-methyl 2-isocyanatopropanoate.

Additional quercetin derivatives include, but are not limited to, compounds that can be described as metabolites formed by the addition of sugar-like derivatives such as glucuronyl groups at any of the hydroxyl positions. Examples of these metabolites include 7-O-glucuronyl-quercetin and 3'-O-glucuronyl-quercetin.

Additional derivatives include, but are not limited to, compounds that arise from the loss of any of the hydroxyl groups of the parent molecule, addition of hydroxyl groups at alternate positions, and any compound that may arise from the previously mentioned reactions to provide a functionalized variant of the dehydroxylated compound.

Quercetin is also a polyphenol present in red wine and it is likewise reported to exert protection against atherosclerosis. From a pharmacological point of view, an exemplary drug combination of the present invention, resveratrol and quercetin, appears reasonable, red wine is actually a combination of low levels of many bioactive polyphenols that act synergistically to exert the effects observed clinically for chronic red wine consumption.

Quercetin is an inhibitor of both platelet and NFκB activation. The addition of quercetin to the DES of the present invention should potentiate the effects of resveratrol on VSMC proliferation by boosting the inhibitory effects on NFκB activation. Further, strong inhibition NFκB should also potentiate resveratrol-mediated inhibition of the inflammatory component of restenosis. Addition of quercetin should also limit platelet activation, which is a part of the inflammatory response to balloon angioplasty and stent implantation that leads to restenosis. Alternatively, another agent or agents which inhibit platelet activation and/or aggregation could be utilized in place of quercetin with resveratrol. Such alternative options include, but are not limited to, aspirin, ticlopidine, clopidogrel, dipyridamole, and the like.

In some aspects, the quercetin used is an acetylated quercetin. Without wishing to be bound by a particular theory, it is possible that acetylated quercetin can permit maintenance of quercetin drug levels at a tissue site with a time course similar to resveratrol or acetylated resveratrol.

Structures of exemplary quercetin derivatives are shown below in Formulas IX-XII.

Formula IX

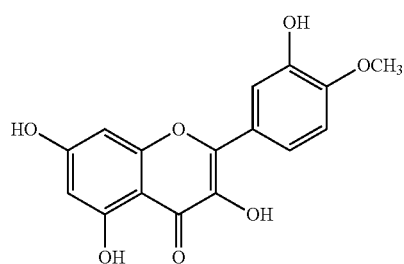

Formula X

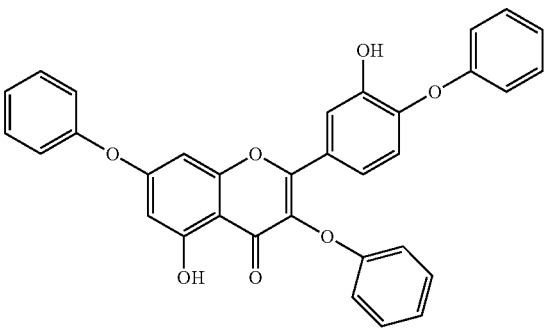

Formula XI

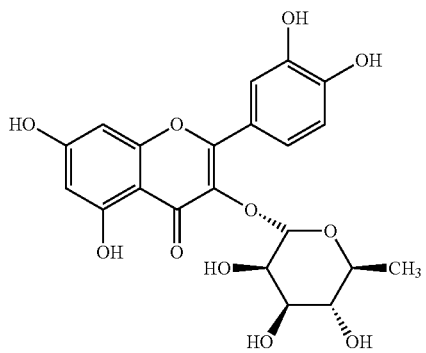

Formula XII

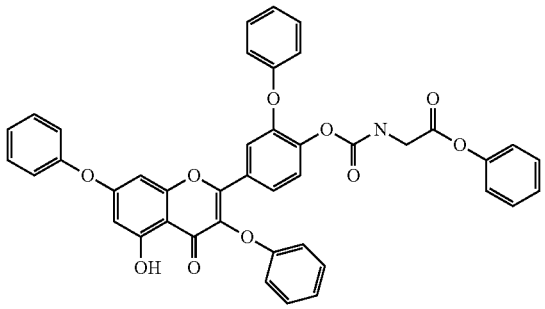

E. RESVERATROL AND QUERCETIN

In various aspects, the disclosed therapeutic agent comprises a first therapeutic agent selected from the group consisting of resveratrol, pharmaceutically acceptable salts, and pharmaceutically acceptable derivatives thereof and optionally a second therapeutic agent selected from the group consisting of quercetin, pharmaceutically acceptable salts, and pharmaceutically acceptable derivatives thereof.

In a further aspect, the first therapeutic agent can be used in combination with a lower amount of the second therapeutic agent. In a still further aspect, the first therapeutic agent is present in a ratio to the second therapeutic agent of from about 1:1 to about 5:1. In a yet further aspect, the first therapeutic agent is present in a ratio to the second therapeutic agent of from about 1:1 to about 2.5:1. In an even further aspect, the first therapeutic agent is present in a ratio to the second therapeutic agent of from about 1.5:1 to about 2.5:1.

In various aspects, the first therapeutic agent can be used in combination with a lower amount of the second therapeutic agent such that the first therapeutic agent is present in a ratio to the second therapeutic agent of 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1; any combination of the foregoing values; or any range encompassed by two of the foregoing values.

In various aspects, the first therapeutic agent can be used in combination with a lower amount of the second therapeutic agent such that the first therapeutic agent is present in a ratio to the second therapeutic agent of 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50; any combination of the foregoing values; or any range encompassed by two of the foregoing values.

F. DRUG-COATED BALLOONS

The present disclosure also provides a DCB catheter balloon comprises a pNP coating comprising one or more therapeutic agent. In some aspects, the first coating is applied directly on the outer surface of a DCB catheter balloon. Without wishing to be bound by a particular theory, the strong ionic interaction between the pNP composition comprising one or more therapeutic agent and the phospholipid layer should overcome the adsorption forces holding the pNPs to the balloon. Such strong ionic interactions can provide a trigger to achieve a detachment of the pNP from the balloon within the limited contact time during inflation.

In a further aspect, the present disclosure pertains to an implantable medical device, comprising: an expandable balloon catheter having an outer surface; and an adherent layer on the balloon catheter comprising a pNP comprising a therapeutic agent selected from the group consisting of resveratrol, pharmaceutically acceptable salts, and pharmaceutically acceptable derivatives thereof, wherein the pNP encapsulates the therapeutic agent.

In a further aspect, the present disclosure pertains to an implantable medical device, comprising: an expandable balloon catheter having an outer surface; and an adherent layer on the balloon catheter comprising a pNP comprising a therapeutic agent selected from the group consisting of quercetin, pharmaceutically acceptable salts, and pharmaceutically acceptable derivatives thereof, wherein the pNP encapsulates the therapeutic agent.

In a further aspect, the present disclosure pertains to an implantable medical device, comprising: an expandable balloon catheter having an outer surface; and an adherent layer on the balloon catheter comprising a pNP comprising a first therapeutic agent selected from the group consisting of resveratrol, pharmaceutically acceptable salts, and pharmaceutically acceptable derivatives thereof, and an optional second therapeutic agent selected from the group consisting of quercetin, pharmaceutically acceptable salts, and pharmaceutically acceptable derivatives thereof, wherein the pNP encapsulates the first therapeutic agent and the second therapeutic agent.

In a further aspect, the present disclosure pertains to an implantable medical device, comprising: an expandable balloon catheter having an outer surface; and an adherent layer on the balloon catheter comprising a pNP comprising a first therapeutic agent selected from the group consisting of resveratrol, pharmaceutically acceptable salts, and pharmaceutically acceptable derivatives thereof, and a second therapeutic agent selected from the group consisting of quercetin, pharmaceutically acceptable salts, and pharmaceutically acceptable derivatives thereof, wherein the pNP encapsulates the first therapeutic agent and the second therapeutic agent.

In various aspects, the DCB catheter balloon consisting of a suitable medical grade polymer with a suitable combination of strength, flexibility and friction characteristics. In some aspects, the balloon comprises a nylon. In a further aspect, the balloon comprises a polyamide block copolymer obtained by polycondensation of a carboxylic acid polyamide (PA6, PA11, PA12) with an alcohol termination polyether (Polytetramethylene glycol PTMG), PEG). Exemplary nylons include those available under the tradenames PEBAX® polyether block amide (Arkema) and VESTAMIDOE® polyether block amide (Evonik Industries). In a further aspect, the DCB catheter balloon comprises one or more polymers possessing a negative zeta potential, e.g., a nylon block copolymer such as a PEBAX® polyether block amide. In alternative aspects, the DCB catheter balloon comprises one or more of a polyethylene, polyurethane, polypropylene and similar materials.

In various aspects, the balloon can be smooth-walled, or in some aspects provided with grooves or with pores, provided in part increase the surface area of the balloon portion. The DCB catheter balloon is typically expandable up to a predetermined size and should preferably be pressure resistant in order to be able expand stenotic arteries back to their original diameter.

In a further aspect, the DCB catheter balloon can optionally further comprise a first coating comprising one or more layers comprising one or more polymer coating material. In some aspects, the first coating is applied to the outer surface of a DCB catheter balloon, and there upon applied the pNP coating. In various aspects, the first coating can comprise one or more of poly L-Lactide polymer (PLLA), poly (lactide-co-glycolide) (PLGA), poly(l-lactide-co-trimethylene carbonate), poly(d,l-lactide-co-trimethylene carbonate), polyvinyl alcohol (PVA) and polyalkylene glycols (PAG) such as polyethylene glycol (PEG), albumin, gelatin, starch, cellulose, dextrans, polysaccharides, fibrinogen, poly(D,L lactide), poly(D,L-lactide-co-glycolide), poly(glycolide), poly(hydroxybutyrate), poly(alkylcarbonate), and poly(orthoesters). The selected polymer coatings can be mixed, combined or covalently bound to the selected bioactive drug in any desired concentration of selected drug. Two or more polymers can be combined with each other to form a polymer matrix used in the second coating. The second coating can comprise multiple coatings or layers of such polymers.

In a further aspect, the DCB catheter balloon can optionally further comprise a second coating comprising one or more layers comprising one or more polymer coating material. In some aspects, the second coating is applied to the pNP coating. In a still further aspect, a DCB catheter balloon can be coated with a first coating on the surface of a DCB catheter balloon, then coated with the one or more layers of a disclosed pNP comprising one or more therapeutic agent, and then further coating with the second polymer coating. Alternatively, a DCB catheter balloon can be coated on the outer surface of the balloon with the pNP coating, and then coated with the second coating there upon. In various aspects, the second coating can comprise one or more of poly L-Lactide polymer (PLLA), poly(lactide-co-glycolide) (PLGA), poly(l-lactide-co-trimethylene carbonate), poly(d, l-lactide-co-trimethylene carbonate), polyvinyl alcohol (PVA) and polyalkylene glycols (PAG) such as polyethylene glycol (PEG), albumin, gelatin, starch, cellulose, dextrans, polysaccharides, fibrinogen, poly(D,L lactide), poly(D,L-lactide-co-glycolide), poly(glycolide), poly(hydroxybutyrate), poly(alkylcarbonate), and poly(orthoesters). Two or more polymers can be combined with each other to form a polymer matrix used in the second coating. The second coating can comprise multiple coatings or layers of such polymers.

The pNP coating comprises a pNP with one or more therapeutic agents encapsulated therein as disclosed herein. Examples of the one or more therapeutic agents which can be encapsulated in a pNP, which is then included in the pNP coating on the DCB catheter, include but are not limited to, resveratrol and quercetin for use in/on a coating on a balloon catheter.

Dip coating techniques can be used for coating the surface of a balloon although other methods may also be employed such as spray coating or electrospray coating methods. In a further aspect, an electrospray method is used to provide the pNP coating, the first coating, and/or the second coating. Coating is typically comprised of a single layer but may also comprise multiple layers depending on the content and release profile of drug contained in the coating.

In various aspects, the present disclosure pertains to a drug coated balloon catheter, comprising: an expandable balloon having an outer surface; and a nanoparticle coating the outer surface of expandable balloon comprising a disclosed pNP composition such that a concentration of the first active agent based on a surface area of the balloon ranges from about 1 to about 5 $\mu g/mm^2$, and a concentration of the second active agent based on the surface area of the balloon ranges from about 1 to about 5 $\mu g/mm^2$.

In a further aspect, the nanoparticle coating the outer surface of the expandable balloon comprises a disclosed pNP composition at a concentration of the first active agent, in units of $\mu g/mm^2$, is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0; any combination of the foregoing values; or a range encompassed by any two of the foregoing values; and at a concentration of the second active agent, in units of $\mu g/mm^2$, is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0; any combination of the foregoing values.

The disclosed DCB catheter balloons are useful in revascularization, catheterization, balloon expansion and stent delivery procedures and methods described herein. In a stent delivery procedure for example, a drug coated balloon according to the invention may also incidentally deliver drugs to vessel areas that are not situated at the localized situs of implant of a stent. Such incidental delivery of drug from the surface of the balloon is of particular utility for small and tortuous vessel passages leading up to the site of interest. Furthermore, healing and re-endothelialization of stent struts that do not carry antiproliferative agents can be facilitated by the use of drug coated balloons.

With a DCB catheter, the balloon walls contact the vessel walls when inflated, and the drug is released. Therefore, the drug may be released during the actual inflation or when it is in contact with the vessel wall. In practice, a therapeutic amount of the drug is delivered to the vessel wall while limiting or reducing systemic delivery. Thus, on pressurized contact of the surface of the balloon with a blood vessel wall either as a result of stent delivery or otherwise, the pNP comprising a therapeutic agent will adhere to the blood vessel wall surface and release the therapeutic agent over a few seconds, a few minutes, or up to a few hours, e.g., less In various aspects, the dose of the therapeutic agent delivered within the first 3 hours after expansion can be at least about 10% of the drug loading (total content of drug, or the amount of drug per device), at least about 25% of the total drug loading, at least about 50% of the drug loading, and at least about 75% of the total drug loading is released. In some aspects, at least about 10% of the drug loading, at least about 25% of the total drug loading, at least about 50% of the drug loading, and at least about 75% of the total drug loading is released within the first 5 minutes following expansion. In some aspects, the DCB catheter may release not less than 25% of the drug within the first 3 minutes following the initiation of expansion, or not less than 25% of the drug within the first 2 minutes following the initiation of expansion. For a DCB catheter, unreleased drug is the drug remaining on the device if removed from the patient, all of the remainder having been released, and preferably a limited amount (not more than 50% of the total content) is released systemically. The amount of drug that may be released systemically may depend upon the specific pharmacokinetics and pharmacodynamics of the drug disposed on the DCB.

In various aspects, the surface of DCB catheter balloon comprises pNP comprising 0.1 to 15 µg of resveratrol and/or quercetin per square millimeter of device surface, e.g., an expandable balloon outer surface, to enable immediate release of the drug on inflation. In a further aspect, the DCB catheter balloon comprises a first therapeutic agent based on the surface area of the balloon catheter ranges from about 1 to about 5 $\mu g/mm^2$, and the concentration of the optional second active agent based on the surface area of the balloon ranges from about 1 to about 5 $\mu g/mm^2$.

In a further aspect, the nanoparticle coating the outer surface of the expandable balloon comprises a disclosed pNP composition at a concentration of the first active agent, reserveratrol (or pharmaceutically acceptable salt or derivative thereof), in units of $\mu g/mm^2$, is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0; any combination of the foregoing values; or a range encompassed by any two of the foregoing values; and at a concentration of the second active agent, quercetin (or pharmaceutically acceptable salt or derivative thereof), in units of $\mu g/mm^2$, is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0; any combination of the foregoing values.

In various aspects, the release profile for pNP comprising a therapeutic agent on the surface of a DCB catheter, and/or other medical device, is in a time period of between about 20 and about 40 seconds, about 1 min to 100 minutes, about 1 hour to 20 hours, about 1 day to 1 month, about 1 day to 10 days, about 1 day to about 30 days, about 1 day to about 2 months, about 1 day to about 6 months, about 1 day to about 6 months, about 1 day to about 1 year. Non limiting examples of delayed profile coating release an active agent and/or agents over a period of at least one month, at least two months, at least six months, or at least one year, after implantation.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

G. METHODS OF TREATING A VASCULAR DISEASE

The present disclosure also pertains to methods of treating a vascular disease comprising treating a subject with a disclosed drug-coated balloon. In a further aspect, the disclosed methods are methods for treating at least one disease or condition associated with vascular injury or angioplasty. Angioplasty may be performed as part of "revascularization" treatment for "artherosclerosis," which as used herein means diseases in which plaque, made up of cholesterol, fats, calcium, and scar tissue, builds up in the wall of blood vessels, narrowing the lumen and interfering with blood flow. "Revascularization," as used herein means any treatment that re-establishes brisk blood flow through a narrowed artery, including bypass surgery, angioplasty, stenting, and other interventional procedures. Secondary complications following revascularization may include restenosis, neointima, neointimal hyperplasia and thrombosis. "Restenosis," as used herein is defined as the re-narrowing of an artery in the same location of a previous treatment; clinical restenosis is the manifestation of an ischemic event, usually in the form of recurrent angina. "Neointima," as used herein is defined as the scar tissue made up of cells and cell secretions that often forms as a result of vessel injury following angioplasty or stent placement as part of the natural healing process. "Neointimal hyperplasia," as used herein means excessive growth of smooth muscle cells from the inner lining of the artery. After angioplasty and/or stenting, excessive growth of these cells can narrow the artery again. "Thrombosis," as used herein means the formation of a blood clot within a blood vessel or the heart cavity itself and a "thrombus" is a blood clot.

Three pathophysiological phases can be distinguished subsequent to revascularization. Stage I, the thrombotic phase (days 0-3 after revascularization). This stage consists of rapid thrombus formation. The initial response to arterial injury is explosive activation, adhesion, aggregation, and platelet deposition. The platelet thrombus may frequently be large and can grow large enough to occlude the vessel, as occurs in myocardial infarction. Within 24 hours, fibrin-rich thrombus accumulates around the platelet site. Two morphologic features are prominent: 1) platelet/fibrin, and 2) fibrin/red cell thrombus. The platelets are densely clumped at the injury site, with the fibrin/red cell thrombus attached to the platelet mass. Stage II, the recruitment phase (days 3-8). The thrombus at arterial injury sites develops an endothelial cell layer. Shortly after the endothelial cells appear, an intense cellular infiltration occurs. The infiltration is principally monocytes that become macrophages as they leave the bloodstream and migrate into the subendothelial mural thrombus. Lymphocytes also are present, and both types of cells demarginate from the bloodstream. This infiltrate develops from the luminal side of the injured artery, and the cells migrate progressively deeper into the mural thrombus. Stage III, the proliferative phase: (day 8 to final healing). Actin-positive cells colonize the residual thrombus from the lumen, forming a "cap" across the top of the mural thrombus in this final stage. The cells progressively proliferate toward the injured media, resorbing thrombus until it is completely gone and replaced by neointimal cells. At this time the healing is complete. In the pig this process requires 21-40 days, depending on residual thrombus thickness. Smooth muscle cell migration and proliferation into the degenerated thrombus increases neointimal volume, appearing greater than that of thrombus alone. The smooth muscle cells migrate from sites distant to the injury location, and the resorbing thrombus becomes a bioabsorbable "proliferation matrix" for neointimal cells to migrate and replicate. The thrombus is colonized at progressively deeper levels until neointimal healing is complete.

In a further aspect, the disclosed methods can be used to treat these conditions subsequent to revascularization, such as those conditions subsequent to any of the three stages described above, e.g., activation, adhesion, aggregation, platelet deposition, thrombosis, platelet aggregation, proliferation, and neointima.

In a further aspect, the first therapeutic agent and the second therapeutic agent are for the prevention or treatment of restenosis subsequent to angioplasty, such as the inhibition of neointimal hyperplasia subsequent to angioplasty.

In a further aspect, the disclosed methods are directed to the prevention of acute, subacute and chronic secondary complications associated with angioplasty. Such secondary complications subsequent to and/or associated with angioplasty are defined herein above and include, e.g., restenosis, neointima, neointimal hyperplasia, thrombosis and inflammation. In a further aspect, the disclosed methods are directed to treating undesired cell proliferation, which is often a component of many disease processes. Undesired cell growth can be a component of restenosis, the recurrence of stenosis or artery stricture after corrective surgery. Restenosis occurs after coronary artery bypass (CAB), endarterectomy, heart transplantation, or after angioplasty, atherectomy, laser ablation or stenting. Restenosis is the result of injury to the blood vessel wall during the lumen opening procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat angioplasty or other procedure to alleviate the restenosis.

In a further aspect, the disclosed methods provide for delivery of the disclosed therapeutic agents locally to reduce side effects from high dose systemic delivery.

H. ASPECTS

The following listing of exemplary aspects supports and is supported by the disclosure provided herein.

Aspect 1. A polymeric nanoparticle composition comprising a first polymer, a second polymer, a first therapeutic agent, and optionally a second therapeutic agent; wherein the first polymer is an acrylate polymer comprising one or more positively charged moieties per polymer chain; wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone); wherein the first therapeutic agent is selected from the group consisting of resveratrol, pharmaceutically acceptable salts, and pharmaceutically acceptable derivatives thereof; and wherein the second therapeutic agent is quercetin, pharmaceutically acceptable salts, and pharmaceutically acceptable derivatives thereof.

Aspect 2. The polymeric nanoparticle composition of Aspect 1, wherein the first polymer is a copolymer comprising acrylate.

Aspect 3. The polymeric nanoparticle composition of Aspect 2, wherein the copolymer comprising acrylate comprises about 60% by weight methyl methacrylate, 30% by weight ethyl acrylate and 10% by weight 2-trimethylammoniumethyl methacrylate chloride.

Aspect 4. The polymeric nanoparticle composition of any one of Aspect 1-Aspect 3, wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone).

Aspect 5. The polymeric nanoparticle composition of Aspect 4, wherein the second polymer is a poly(lactide-co-glycolide).

Aspect 6. The polymeric nanoparticle composition of any one of Aspect 1-Aspect 5, wherein first therapeutic agent is triacetyl resveratrol.

Aspect 7. The polymeric nanoparticle composition of any one of Aspect 1-Aspect 6, wherein second therapeutic agent is quercetin.

Aspect 8. The polymeric nanoparticle composition of any one of Aspect 1-Aspect 7, wherein the first therapeutic agent and the second therapeutic agent are present in a ratio of about 1:1 to about 1:5.

Aspect 9. The polymeric nanoparticle composition of any one of Aspect 1-Aspect 8, comprising nanoparticles having a diameter of about 100 nm to about 300 nm.

Aspect 10. The polymeric nanoparticle composition of any one of Aspect 1-Aspect 9, wherein comprising nanoparticles having a pH-independent zeta potential of about 0.35 mV to about 0.60 mV.

Aspect 11. A drug coated balloon catheter, comprising: an expandable balloon having an outer surface; and a nanoparticle coating the outer surface of expandable balloon comprising a disclosed pNP composition of any one of Aspect 1-Aspect 10, wherein a concentration of the first active agent on at least a portion of the outer surface of the expandable balloon ranges from about 1 to about 5 µg/mm$^2$, and a concentration of the second active agent based on the surface area of the balloon ranges from about 1 to about 5 µg/mm$^2$.

Aspect 12. The drug coated balloon catheter of Aspect 11, wherein the balloon outer surface comprises a polyamide block copolymer.

Aspect 13. A method for treating a vascular disease comprising treating a subject with the drug coated balloon catheter of any one of Aspect 11-Aspect 12.

Aspect 14. A kit comprising a drug coated balloon catheter of any one of Aspect 11-Aspect 12 and instructions for using the drug coated balloon catheter to treat a vascular disease.

Aspect 15. A kit comprising a polymeric nanoparticle composition of any one of Aspect 1-Aspect 10, instructions for coating the polymeric nanoparticle composition on an expandable balloon, and: (a) a balloon catheter comprising an expandable balloon; or (b) an expandable balloon suitable for use with a balloon catheter.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

I. EXAMPLES

Now having described the aspects of the present disclosure, in general, the following Examples describe some additional aspects of the present disclosure. The following examples to be purely exemplary of the disclosure and are not intended to limit the scope of what the inventors regard as their disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. Method for Nanoparticle Synthesis

In the example described herein, and other examples described herein below, certain materials were used in the studies and obtained as follows: Resomer® RG504H poly (lactic-co-glycolic acid) PLGA 50:50, quercetin (QUER), and acetonitrile were obtained from Sigma Aldrich Corp. (St. Louis, MO); ethyl acetate, Tween 80, resveratrol (RESV) and triacetate resveratrol (TAR) were obtained from Thermo Fisher Scientific (Waltham, MA); and EUDRAGIT® RL100 ammonio methacrylate copolymer was obtained from Evonik Industries AG (Essen, Germany). The polymeric nanoparticle synthesis followed a single emulsion evaporation technique (Astete C. E. and Sabliov C. M. J. Biomater Sci Polym Ed. 2006; 17(3):247-89).

Briefly, an organic phase was created by mixing EUDRAGIT® RL-100 ammonio methacrylate copolymer (60 mg) and PLGA (200 mg) in ethyl acetate to acetone (8:2) solution (6 mL), with mild stirring at room temperature for 30 min. Next, a 1:2 molar ratio of quercetin and triacetate resveratrol (TAR) was added to the organic phase. Acetylated resveratrol was utilized after pilot studies demonstrated its entrapment efficiency was greater than that of resveratrol. Moreover, the 1:2 molar ratio was shown to invoke the greatest biologic synergy between the compounds in our prior studies. 12 After 15 min and with continued stirring at room temperature, the organic phase was poured drop-wise into 60 mL of aqueous phase containing 4 mg/mL Tween 80. To reduce the droplet size, the emulsion was microfluidized with a Microfluidizer M-110P (Microfluidics Corp, Westwood, MA) at 4° C., 30,000 PSI, and with four passes. Ethyl acetate in the suspension was evaporated using a Rotavapor Buchi R-300 (Buchi Corp., New Castle, DE) under vacuum at 32° C. for 2 h. Finally, the nanoparticle suspension was mixed with trehalose at a 1:2 mass ratio, and the suspension was freeze-dried with a FreeZone 2.5 (Labconco Corp., Kansas City, MO) at −80° C. for 2 d. A 2 mL solution of polyvinyl alcohol (PVA) (30 mg) was added before freeze-drying to minimize aggregation after polymeric nanoparticle resuspension. The powdered samples were kept at −20° C. until further characterization and use.

Example 2. Method to Determine Drug Loading and Entrapment Efficiency

Drug loading and entrapment efficiency were determined using HPLC. Standard curves were first made in the extraction solvent dimethylformamide (DMF). Initial testing indicated that quercetin required ascorbic acid to minimize its degradation while TAR was analyzed in DMF without the addition of ascorbic acid. Drug loading was measured by suspending loaded polymeric nanoparticles in DMF at a concentration of 3.9 mg/mL. Samples of 200 µL each were collected, and 80 µL of ascorbic acid was added to each. The samples were clarified using centrifugation, then analyzed using HPLC. The sample that had ascorbic acid was analyzed for quercetin, while the one without was analyzed for TAR and resveratrol. Analysis was performed in triplicate. Theoretical loading was calculated relative to the initial amounts of quercetin and TAR added during synthesis.

Example 3. Method for Assessment of Drug Release Profile

A drug release profile was performed to measure the release of both drugs from the pNP over a 10-d period. The release study was performed in simulated blood solution at a pH of 7.4 to mimic physiological conditions. Nanoparticles were suspended at a concentration of 19.5 mg/L. This suspension was transferred to a dialysis bag which was sealed and placed in the simulated blood solution. 13 The whole system was placed in a rocking incubator for 10 d. Each day, a sample was collected from inside the dialysis bag, and the samples were analyzed by HPLC using a protocol similar to that used to determine drug loading.

Example 4. Method of Cell Uptake of Drug

Rat aortic smooth muscle cells were grown to confluency in six well plates. For the first group, the cells were treated quercetin (QUER) or TAR at 12.5 and 25 µM, respectively, aiming for a 1:2 molar ratio shown to exhibit maximal synergy in prior studies. [12] For the second group, the cells were treated with 1.4 mg/mL pNP containing entrapped QUER and TAR. After treatment, the cells were incubated for six hours, as preliminary studies indicated this was where maximal uptake occurred. Methanol and ascorbic acid were used to precipitate the protein and retain all other components of the cell. HPLC was performed to determine the amount of quercetin and TAR present in the cell and the data were normalized to cell protein, quantified using the BCA protein assay.

Example 5. Method for Quantitation of Drug Levels

Drug release from the nanoparticles and within cells was quantified with reverse-phase HPLC, using a Waters 2695 Alliance separation module (Milford, MA) coupled to a Waters 2487 dual wavelength absorbance detector and a 4-channel ESA 5600A CoulArray electrochemical detector (Chelmsford, MA). The separation was achieved using a Targa C18 3 µm 150×4 mm column (Higgins Analytical, Mountain View, CA). Mobile phase A consisted of 10:90 acetonitrile/water containing 75 mM citric acid and 25 mM ammonium acetate. Mobile phase B was 50:50 acetonitrile/water containing 75 mM citric acid and 25 mM ammonium acetate. The phases were applied to the column at 0.53 mL/min using the following linear gradient: 70% A/30% B to 10% A/90% B over 35 min, 10% A/90% B for 12 min, followed by re-equilibration to initial conditions over the next 3 min. QUER was quantified by peak areas detected on the 200, 580 and 750 mV channels combined. TAR was quantified on the 750 mV channel. RESV was detected and quantified on the 100, 200, 580 and 750 mV channels, combined. Sample peaks were matched with authentic standards on the basis of their retention times.

Example 6. Method for Assessment of Biocompatibility

The lysis of red blood cells in the presence of pNP was used as a measure of biocompatibility. For the hemolytic assay, 14 polymeric nanoparticles containing triacetyl resveratrol (TAR) and quercetin were used. The nanoparticle solution was diluted using PBS to the following concentrations: 0.1, 0.3, 0.9, 1.5, and 2.0 mg/mL. The blood used was taken from mice sacrificed for other studies approved by the Institutional Care and Use Committee at the Louisiana State University School of Veterinary Medicine. Assuming a hemoglobin concentration in blood of 140 mg/mL, the blood was diluted to 10 mg/mL using PBS. Next, 700 μL of PBS, 100 μL of diluted blood, and 100 μL of each nanoparticle concentration were combined. For the positive control, 100 μL of 10% Triton X solution was added instead of the nanoparticle solution. Furthermore, the negative control lacked the nanoparticle solution. The samples were then placed in a 37° C. water bath for about 3 hours. Following incubation, the samples were centrifuged for 15 min at 800×g at room temperature. After centrifugation, 100 μL of the supernatant from each sample was placed in a 96 well plate in triplicate. Next, 100 μl of cyanmethemoglobin was added to each well and the samples were incubated for 10 minutes. A standard curve was created using the cyanmethemoglobin reagent. 14 A serial dilution of the reagent was made using phosphate-buffered saline (PBS), covering a concentration range of 1-150 mg/mL. 200 μL of each diluted sample was added to a 96 well plate in triplicate. A Biotek Citation 3 spectrophotometer (Winooski, VA) was used to measure the absorbance of the samples at 532 nm. Finally, absorbance was measured using the BioTek spectrophotometer at 532 nm.

Example 7. Method for Determination of Cytotoxicity

A Luminescent Cell Viability Assay (Promega, Madison, WI) assessing relative levels of ATP was performed in order to test the cytotoxicity of the nanoparticle assay. Rat aortic smooth muscle cells were plated in opaque-walled 96 well plates in culture medium to be tested at four separate time-points. After growing to confluency, the first group of cells was treated with the original nanoparticles at concentrations of 0.1 mg/mL, 0.3 mg/mL, 0.9 mg/mL, 1.5 mg/mL, and 2.0 mg/mL and the second group of cells was treated with nanoparticles at a concentration of 0-1.5 mg/mL. Each concentration of nanoparticles was tested in triplicates, and the experiment was performed three times. At 6, 24, 48, and 72 h of incubation, the plates were taken out of the incubator to sit at room temperature for thirty minutes. The Cell Titer-Glo® Reagent, a lyophilized enzyme/substrate mixture, was added to each well. The contents were mixed for 2 min on an orbital shaker to induce cell lysis. The plate was incubated at room temperature for 10 min to stabilize the luminescent signal. Luminescence was then recorded on a Biotek Synergy microplate reader.

Example 8. Characterization of Nanoparticles Comprising QUER and RESV

Exemplary nanoparticles were prepared using the method described herein above, and characterized using the various methods described herein above. A exemplary nanoparticle composition containing entrapped QUER and RESV presented a spherical shape with narrow size distribution (FIG. 1). The nanoparticles had a mean size of 185±12 nm after resuspension in ultrapure water with a zeta potential of +48±4.5 mV (Table 1). Without wishing to be bound by a particular theory, it is possible that the positive zeta potential is due to the amino alkyl side groups of the methacrylate polymer (EUDRAGIT® RL100 ammonio methacrylate copolymer).

TABLE 1

| Characteristics of QUER:TAR-entrapped pNP. | |
|---|---|
| Size (nm) | 185 ± 12.5 |
| PDI | 0.105 |
| Zeta (mV) | +48 ± 4.5 |
| Entrapment efficiency (%) | 34.4 (Q) and 63.3 (TAR) |
| Entrapment loading (g/mg powder) | 5.68 (Q) and 7.04 (TAR) |
| Entrapment Ratio | 1 : 1.09 Q:TAR |

Theoretical loading was calculated relative to the initial amounts of QUER and TAR added during synthesis. Drug loading, entrapment efficiency, and molar ratio of QUER to TAR were then calculated (Table 1). The observed ratio (1:1.09) was close to meeting the design objective of a 1:2 molar ratio of QUER:TAR.

Figure 2:
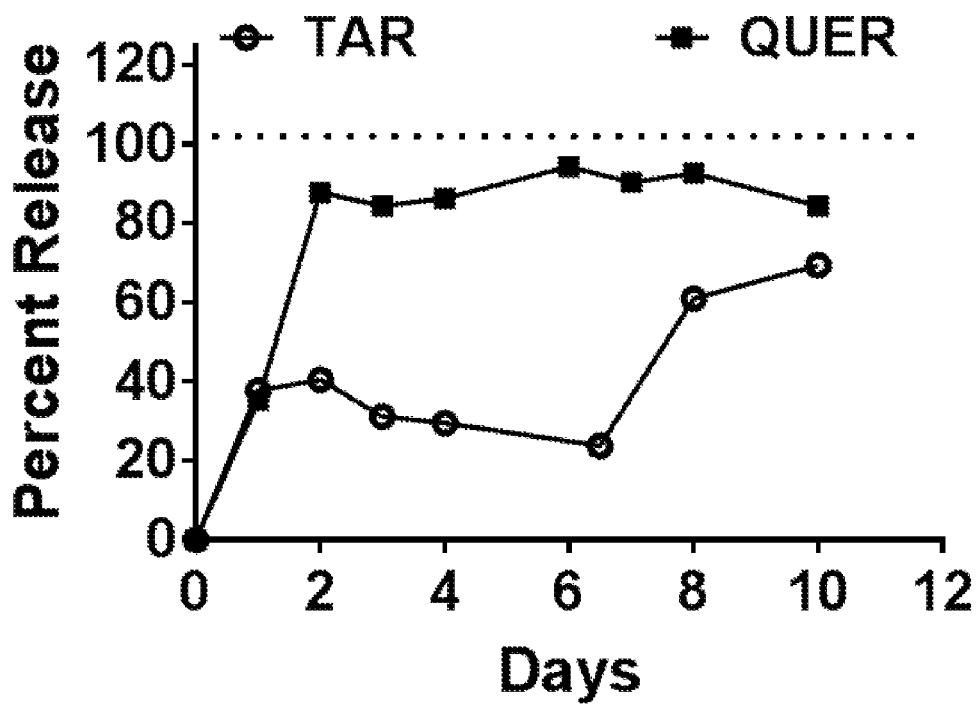
FIG. 2 shows representative drug release data for the release of triacetyl resveratrol and quercetin (labeled as "TAR" and "QUER," respectively, in the figure) from a representative disclosed poly(D,L-lactide-co-glycolide)/cationic polymethacrylate nanoparticle composition (nanoparticles are indicated as "pNP" in the figure). Levels of triacetyl resveratrol (TAR), reserveratrol (labeled as "RESV" in the figure), and quercetin (QUER) diffusing outside a dialysis membrane were assessed by high performance liquid chromatography using methods described herein below. Data are means±SEM for n=6.

For the drug release profile measured over 10 days, 82% of the quercetin and 76% of the pNP-entrapped TAR was released by day 10. Though both drugs demonstrated a burst release within the first day, the pNP continued to release both drugs over the entire 10-d period (FIG. 2).

Figure 3:
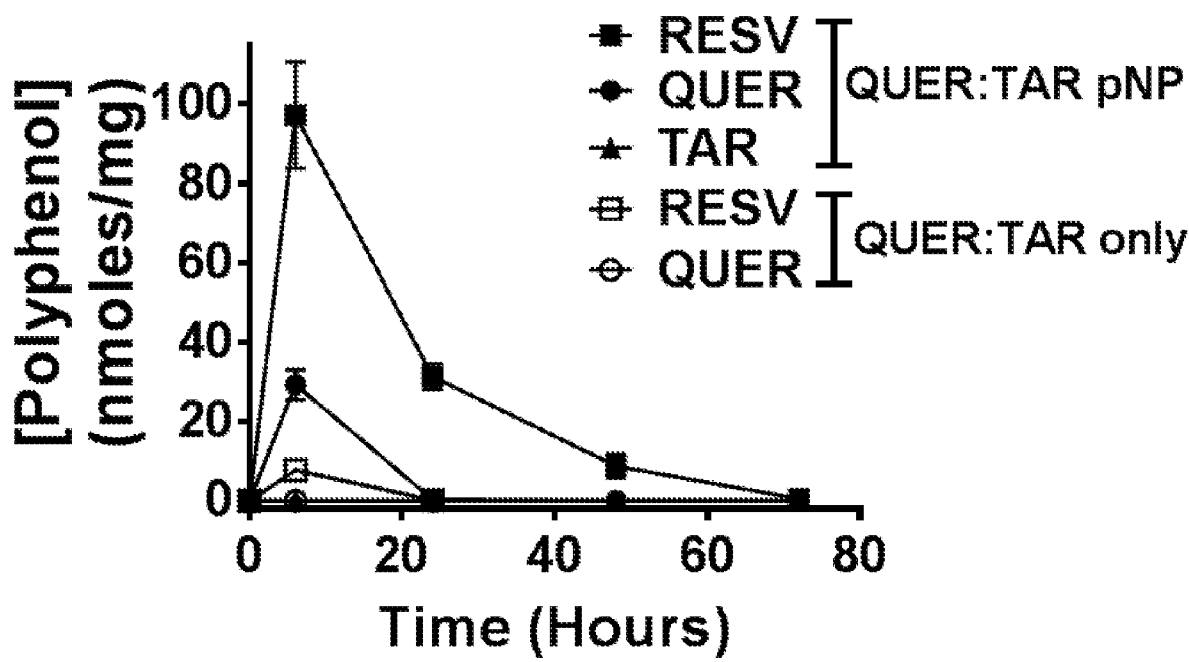
FIG. 3 shows representative cellular uptake data for the uptake by vascular smooth muscle cells of triacetyl resveratrol, resveratrol and quercetin (labeled as "TAR," "RESV," "QUER," respectively, in the figure) from a representative disclosed poly(D,L-lactide-co-glycolide)/cationic polymethacrylate nanoparticle composition (nanoparticles are indicated as "pNP" in the figure). The vascular smooth muscle cells were loaded with either the nanoparticles comprising the triacetyl reserveratrol and quercetin or exposed to triacetyl resveratrol and quercetin alone. The cells were then extracted and analyzed by HPLC at 0-72 h for drug levels (triacetyl resveratrol, reserveratrol, and quercetin). Data are means±SEM for n=3 experiments.

Although resveratrol was not used to treat the cells, acetylated drugs are known to undergo ester hydrolysis within cells through the action of resident esterases (Davis, B. H., et al., Int J Lab Hematol. 2010. 32(2):139-41). Thus, not surprisingly, RESV, rather than TAR itself, was observed by HPLC at 6 h. The cells treated with the polyphenol-entrapped pNP exhibited a higher amount of intracellular RESV, QUER, and TAR than the cells undergoing direct drug treatment without nanoparticles (FIG. 3). To more comprehensively compare cellular uptake of drugs utilizing the pNP compared to direct drug treatment, areas under the curve (AUC) for each analyte were calculated using Graph-Pad Prism version 6 software (La Jolla, CA). The resulting AUC were ~2040 and 361 for RESV and QUER, respectively, when the drugs were delivered entrapped within pNP, but were 94.4 and 0.0116, when the drugs were delivered without pNP. Thus, entrapment using pNP enhanced drug delivery to the cells by >20-fold for RESV and by >4 orders of magnitude for QUER.

Figure 4:
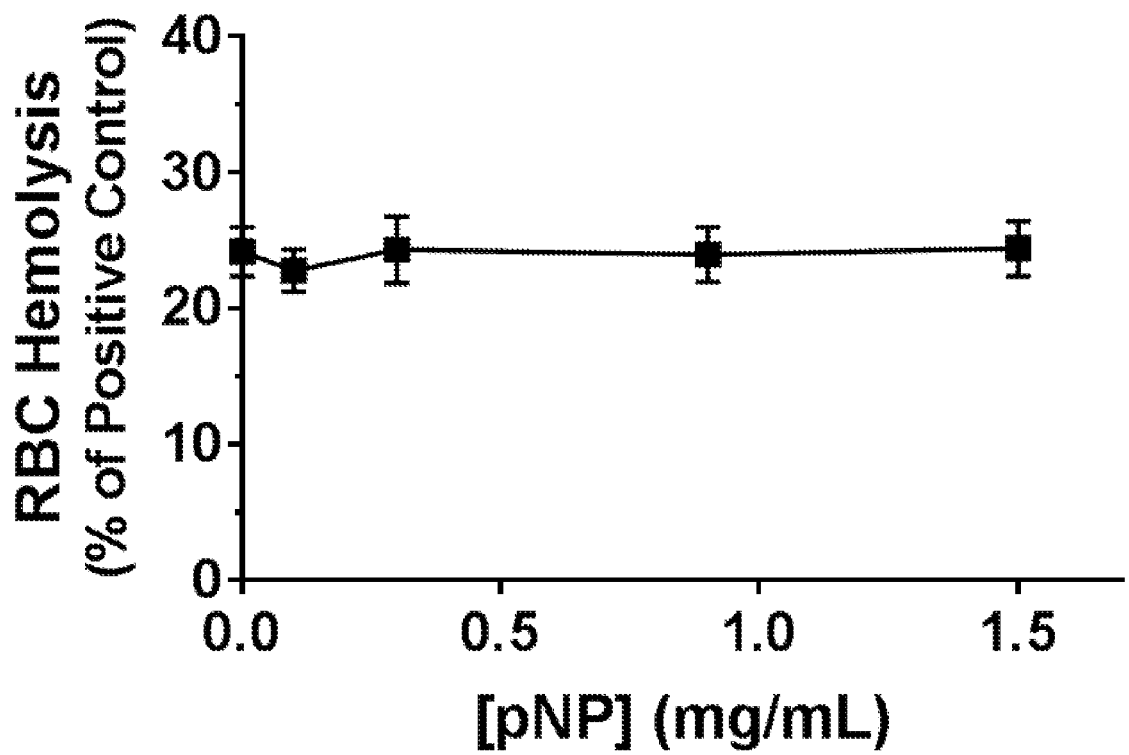
FIG. 4 shows representative biocompatibility data for a representative disclosed poly(D,L-lactide-co-glycolide)/cationic polymethacrylate nanoparticle composition comprising triacetyl resveratrol and quercetin. Biocompatibility was determined as % RBC lysis compared to a positive control (Triton-X100) for the indicated concentrations of nanoparticles. Data are means±SEM for n=3 experiments. ANOVA revealed no significant effect.

Biocompatibility was assessed as the ability of the polyphenol-entrapped pNP to increase the hemolysis of red blood cells. At none of the doses tested (0-1.5 mg/mL) did hemolysis in the presence of drug entrapped pNPs exceed that of the vehicle, which was about 24% at baseline (FIG. 4).

Figure 5:
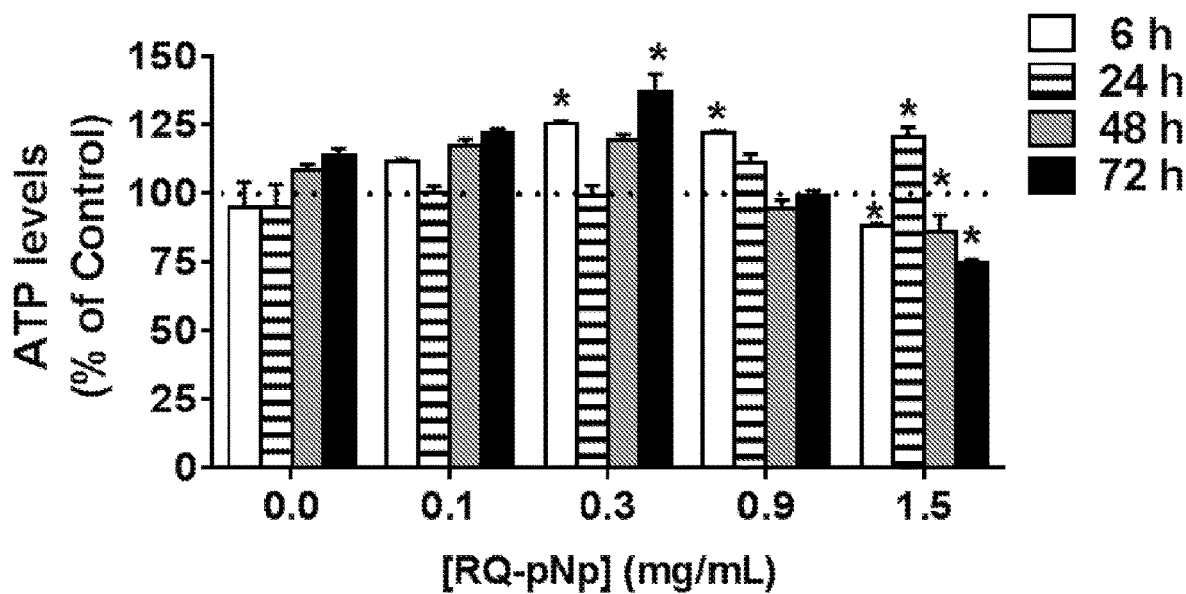
FIG. 5 shows representative cell viability data following treatment with representative disclosed poly(D,L-lactide-co-glycolide)/cationic polymethacrylate nanoparticle composition comprising triacetyl resveratrol and quercetin. Cell viability was assessed in terms of cellular ATP levels at 6-72 hours. ATP levels are expressed as a percent of control (no nanoparticle treatment). Data are means±SEM for n=3 experiments. *p<0.05 compared to controls.

Whether the polyphenol-entrapped pNP altered cell viability was assessed in smooth muscle cells, since these are the cells intimately associated with the particles, as the balloon denudes the endothelium on inflation. Viability, assessed as ATP levels compared to cells with no pNP treatment, was maintained or even increased at most doses. At the 1.5 mg/mL concentration, however, ATP levels were decreased by 12-24% at the 6, 48 and 72 h time points (FIG. 5). Nevertheless, it is not anticipated that for clinical use pNP concentrations would reach this level in the blood.

In the studies described herein, nanoparticles comprising a polyphenol composition have been characterized. These nanoparticles provide a novel nanoentrapped drug-eluting delivery system suitable for a balloon catheter. The nanoparticles comprising the described polyphenol composition is ideal to provide an alternative treatment for PAD that minimizes the risks currently associated with drug coated balloons (DCB) utilizing paclitaxel and other antimitotic agents. It is important to note that the necessary nanoparticle size to ensure endocytosis, as recommended by Panyam and Labhasetwar (Panyam J. and Labhasetwar V. Pharm Res. 2003. 20(2):212-20.) is 100 to 500 nm. The disclosed pNP produced in described herein averaged 185 nm in size and thus are predicted to be endocytosed by cells. Based on the disclosure herein, the conditions and methods can be further optimized to adjust the drug loading to a 1:2 QUER:TAR ratio. The nanoparticles synthesized and tested have been shown herein to be biocompatible with minimal cytotoxicity. Moreover, the disclosed nanoparticles have been shown herein to be ideal for cellular uptake and provide an extended period of release. Note that release kinetics of ≥10 days, as was demonstrated herein, is ideal for these devices, because the cellular events promoting restenosis typically occur within the first 10-14 days after angioplasty (Finn, A. V., et al., Arterioscler Thromb Vasc Biol. 2007. 27(7):1500-10).

Example 9. Prospective Electrospray Process for Coating Balloon

Polyphenol entrapped pNPs comprising RESV and QUER will be synthesized as described herein above. Balloon catheters will be coated with pNPs using electrospray and dried. The coating quality will be characterized using spectroscopy and SEM and using HPLC measures of total drug loading and release.

To optimize the pNP attachment to the balloon, a balloon polymer often used commercially, PEBAX® polyether block amide, possessing a negative zeta potential, will be initially selected. The electronegativity of PEBAX® polyether block amide should provide a good matrix for attachment of the positive-charged TAR:Q-entrapped pNPs. A pNP can be applied by dip coating or electrospray methods. Electrospray methods can be utilized with various chemical and biological agents, offers increased uniformity, allows several layers to be applied, and is already being used with >60 solvents, pharmaceutical compounds, and polymers in the biomedical field.

Figure 6:
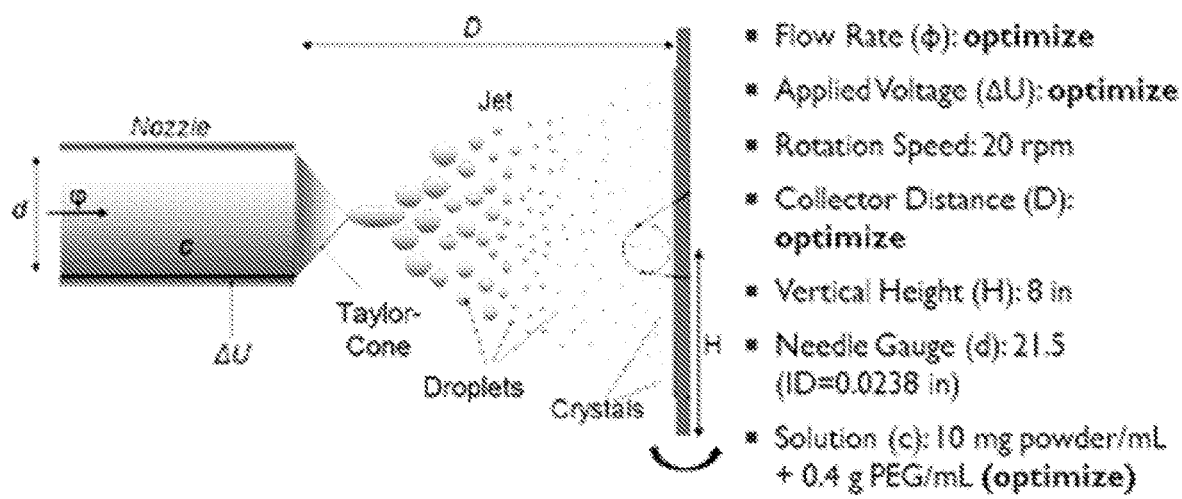
FIG. 6 shows a representative electrospray system for coating a DCB catheter balloon with a coating comprising a disclosed pNP comprising one or more therapeutic agent. The figure shows typical parameters that can be varied to optimize coating characteristics.

Electrospray uses the electrical energy from a voltage source to excite molecules in solution to enter a gas phase. The main physical components in the electrospray system are a voltage source, a syringe pump, and a grounded rotary collector. The three steps involved in transferring the molecules into a gaseous state include charging the droplets to achieve a fine spray, evaporation of the solvent in the solution (using a drying gas), and ejection of the ions from the positively charged droplets. To vary the particle size, the flow rate, voltage supply, collector distance, and solution viscosity can be altered (FIG. 6). Dry, almost dry, or wet coatings can be achieved by increasing or decreasing the collector distance, allowing for an assortment of surface profiles.

As shown in FIG. 6, a solution containing TAR:QUER-entrapped pNPs and polyethylene glycol (PEG; to enhance solution viscosity) can be applied with a constant flow rate through a Taylor cone, to which a voltage is applied, such that the particles possess a charge. As the droplets move through the electric field away from the cone tip and with an applied inert gas, the droplets become desolvated and as a result, increasing smaller. They are finally attracted to an area of opposite charge, in this case, the balloon surface, where they deposit. The balloon catheter is rotated during the spraying process, such that a uniform coating is applied to all sides, and after spraying, the balloon is allowed to dry in a flow hood.

Figure 7A:
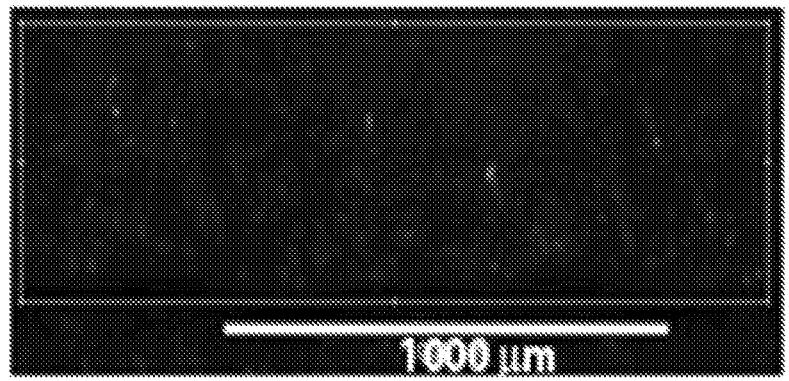
FIGS. 7A and 7B show representative fluorescent micrographs of a DCB catheter balloon coated by dip-coating (FIG. 7A) or electrospray coating (FIG. 7B). The coating in each case was a pNP composition comprising RESV and QUER. The balloon material comprised PEBAX® polyether block amide.

Pilot studies demonstrated that the TAR:QUER-entrapped pNPs were fluorescent, enabling our ability to determine surface coverage using fluorescence imaging and analysis using ImageJ software. TAR:Q-entrapped pNPs were synthesized and then either electrosprayed or dip-coated onto balloon catheters and then allowed to dry under a flow hood. The balloons were removed from their catheters and imaged using fluorescence microscopy. Selecting fields of equivalent sizes, a distribution plot correlating with the brightness of green fluorescence in a given field was constructed. Fluorescence intensities were much greater for the electrosprayed surface, with only minimal intensity observed for the dip-coated DCB. After analyzing all segments of each balloon, the percent coverage was calculated. In comparison to the dip coated balloon (FIG. 7A), electrosprayed balloons (FIG. 7B) produced approximately 65% greater surface coverage, with 70% of the balloon covered with TAR:QUER-entrapped pNPs.

A single emulsion evaporation technique as described above can be used to synthesize pNPs. The process involves two phases—aqueous and organic. The organic phase will be created by mixing EUDRAGIT® RL 100 ammonio methacrylate copolymer and PLGA in ethyl acetate:acetone solution under mild stirring at room temperature for 20 min. Next, a 1:2 molar ratio of QUER and TAR will be added to the organic phase. After stirring, the organic phase will be poured drop-wise to the aqueous phase with Tween 80 under stirring at room temperature. Next, the emulsion will be microfluidized to reduce the droplet size with a Microfluidizer at 4 to 8° C. with three passes. The organic solvents will be evaporated under vacuum at 32° C. for 2 h. Finally, the NP suspension will be mixed with trehalose, freeze dried and storage at −80° C. Polyvinyl alcohol will be added before freeze-drying, along with a sugar cryoprotectant to minimize aggregation.

The pNP system will be loaded with TAR and QUER, and pNP characterization will be performed using FTIR, H-NMR, DLS, and TEM. Drug loading and release kinetics will be measured under physiologically relevant conditions using an HPLC method similar to that described herein above. Briefly, samples will be injected onto a Waters 2695 HPLC System interfaced to an ESA Coularray 4-channel electrochemical detector. Analytes will be separated using a gradient separation we described previously.

Figure 7B:
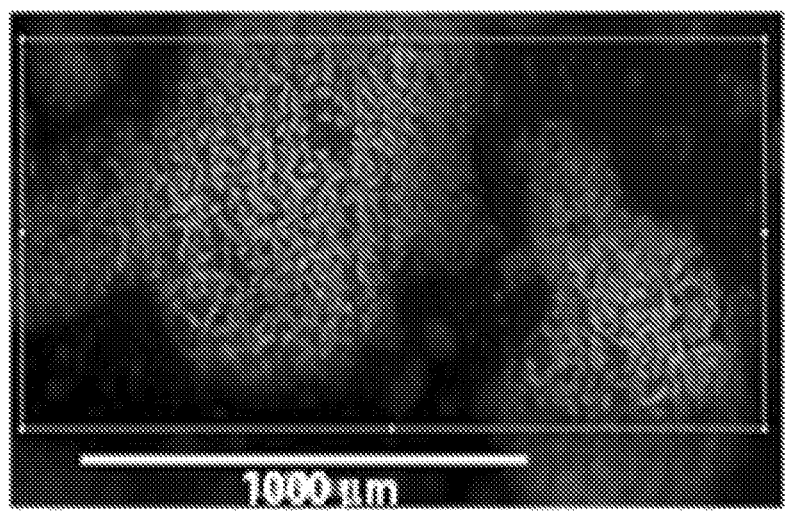

A solution-filled Hamilton syringe will be placed on the syringe pump and the source situated at a desired collector distance. The electrospray nozzle will be interfaced to a voltage source for exciting the molecules in solution. A ground will be applied. The balloon will be affixed to an arduino supplying a constant rotational speed. As shown in FIG. 6 solution flow rate, viscosity (adjusted using PEG), voltage, rotation speed, collector distance, etc., will be modified to provide a uniform coating with maximal drug loading. As described above in the preliminary studies, a ~70% coverage has already been achieved (FIG. 7B).

The balloon coating will be examined under SEM using instrumentation in place in the Shared Instrumentation Facility at LSU. Coverage, uniformity and cracking will be assessed by observation of images across multiple fields per balloon and for up to 14 d after coating and drying. Uniformity will be calculated using the fluorescence imaging technique a described above.

. Four different quality tests will be performed. (1) From a subset of 5 balloons, the drug-entrapped pNPs will be removed using ethanol, and then injected onto HPLC for measurements of total drug loading (typically, drug loading for DCB products is ~2-3 µg/mm$^2$); (2) 5 balloons each will be sectioned longitudinally and crosswise, and then eluted with ethanol and evaluated for drug loading (a variability of 10% between sections will be viewed as a success; (3) 5 balloons will be inflated using a balloon inflation device in place in the lab and then shaken, and then the balloons will be extracted of drug-entrapped pNPs using ethanol and the remaining drug loading, determined by injecting the extracts onto HPLC (it should be noted that commercial DCBs demonstrate dry drug loss of up to 11%; thus, we will consider a result of <20% as a positive outcome; and (4) each of 5 balloons will be inserted into a simulated blood solution subjected to flow using a circulating water bath, and drug levels in the solution will be measured at 0-6 h. Considering a transit time of 30 s within an angioplasty procedure, and an inflation time of 2 min, we will consider success as 20% of the drugs remaining on the balloon up to 6 h. This would be a significant advance compared to current DCBs, which lose 80% of drug on transit.

Example 10. Prospective In Vivo Studies in an Animal Model of Balloon Angioplasty A key parameter for a successful DCB is delivery of therapeutically effective levels of a therapeutic agent at biologically appropriate time points. Thus, studies will be carried in an appropriate animal model, i.e., a rat carotid artery model using retired Sprague Dawley breeder animals, to demonstrate levels of drug in and around the balloon inflation site within a critical time window. Key cellular events occurring after angioplasty and promoting restenosis take place within the first 14 d. Optimally, re-endothelialization should also occur within in this window. In the prospective studies, tissue drug levels at 1-14 d after balloon inflation. To keep the cost of these studies low, we will utilize the rat carotid artery model already well-established in the Dugas laboratory. It should be noted that the carotid artery of a retired Sprague Dawley breeder is sufficiently large for inflation of a balloon catheter. Although it may be preferable to use a peripheral artery such as the iliac or femoral, those vessels in the rat are <1 mm in diameter, half the size of the smallest balloon catheter that can be purchased or custom designed. Sometimes, investigators will utilize a Foley embolectomy catheter for studies in rats, but their use would not advance the development of our PEBAX® polyether block amide over-the-wire balloon prototype.

The in vivo animal study will use male and female Sprague Dawley rats, with 12 rats/gp evenly stratified across the sexes. Polyphenol-entrapped pNP coated balloons will be prepared as described herein above. The coated balloons will then be ethylene oxide-sterilized using standard procedures. To limit thrombosis, aspirin will be added to the drinking water starting 1 wk before surgery. Although aspirin may itself alter vascular healing, its use is required to avoid fatal thrombus formation in the injured artery during/after the procedure. On the day of surgery, study animals will be anesthetized using pentobarbital supplemented with isoflurane/$O_2$. The ventral neck region will be shaved and scrubbed. Through a midline incision, the left common, external, and internal carotid arteries will be exposed. A silk suture will be placed under the arteries to block flow for ~5 min. A transverse arteriotomy will be made in the left external carotid artery. The drug-entrapped pNP coated balloon will be advanced into the common carotid, inflated at 10 atm for ~2 min, deflated and withdrawn. The external carotid artery will be ligated distal to the arteriotomy and blood flow will be restored through the common carotid. Heparin will be injected i.p. after restoring blood flow. Muscle fascia and skin will be sutured. Gas anesthesia will be discontinued and the rat will be monitored. At 1, 2, 7, 10 and 14 d, the rats will be euthanized. Blood will be taken from the vena cava, and tissues will be excised and rapid frozen. Per FDA guidance, drug levels will be measured at the site of balloon inflation, in plasma, tissues proximal and distal to the inflation site, in liver, lung, kidney, heart, etc.

Tissues will be homogenized, extracted 2× with methanol, concentrated under $N_2$, and analyzed using the HPLC methods as described herein above, or similar to such methods. It is anticipated that larger concentrations of resveratrol and quercetin will be detected within 1-2 days following the procedure, with lower levels thereafter.

Repeated measures ANOVA using GraphPad Prism software will be applied to assess significant increases in tissue drug levels over time. Using data collected in studies of RQ-eluting drug-eluting stents (DES) implanted in rat carotid arteries, a power analysis with G*Power (Dusseldorf) was conducted previously. Assumptions were: $\alpha=0.05$, effect size=0.5 $\mu g/cm^2$, power=0.9 and 5 measurements. Based on this prior study, it is anticipated that the described study should be able to detect significant increases in tissue drug levels over time with 8 rats/gp. However, 1) it is possible that about 10% of the rats will be lost during surgery, and 2) drug accumulation from a DCB may be less than that of a DES. Thus, the study described herein begins with 12 rats/gp. To ensure rigor in the study approach and reduced bias due to a particular procedural circumstance, these animals will be spread across two surgery trials. It is anticipated that drug accumulation within the vessel wall will not differ with sex. It is important to insure that the data obtained in this prospective study represent the human population, thus, it is proposed to evenly stratify across sexes.

It is anticipated that polyphenols, i.e., RESV and QUER, can be detected for the first few days after angioplasty, but a measurable level at 7 d would be considered extremely positive.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A polymeric nanoparticle composition comprising a first polymer, a second polymer, and a first therapeutic agent; wherein the first polymer is an acrylate polymer comprising one or more positively charged moieties per polymer chain; wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone); and wherein the first therapeutic agent is triacetyl resveratrol.

2. The polymeric nanoparticle composition of claim 1, wherein the first polymer is a copolymer comprising acrylate.

3. The polymeric nanoparticle composition of claim 2, wherein the copolymer comprising acrylate comprises about 60% by weight methyl methacrylate, 30% by weight ethyl acrylate and 10% by weight 2-trimethylammoniumethyl methacrylate chloride.

4. The polymeric nanoparticle composition of claim 1, wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone).

5. The polymeric nanoparticle composition of claim 4, wherein the second polymer is a poly(lactide-co-glycolide).

6. The polymeric nanoparticle composition of claim 1, further comprising a second therapeutic agent, wherein the second therapeutic agent is selected from quercetin, pharmaceutically acceptable salts, and pharmaceutically acceptable derivatives thereof.

7. The polymeric nanoparticle composition of claim 6, wherein the first therapeutic agent and the second therapeutic agent are present in a ratio of about 1:1 to about 1:5.

8. The polymeric nanoparticle composition of claim 6, wherein the second therapeutic agent is quercetin.

9. The polymeric nanoparticle composition of claim 1, comprising nanoparticles having a diameter of about 100 nm to about 300 nm.

10. The polymeric nanoparticle composition of claim 1, wherein the nanoparticles have a pH-independent zeta potential of about 0.35 mV to about 0.60 mV.

11. A drug coated balloon catheter, comprising:
an expandable balloon having an outer surface;
a nanoparticle coating on the outer surface of the expandable balloon, wherein the nanoparticle coating comprises a first polymer, a second polymer, and a first therapeutic agent;
where the first polymer is an acrylate polymer comprising one or more positively charged moieties per polymer chain;
where the second polymer is selected from the group consisting of poly(lactide), poly(glycolide), poly (lactide-co-glycolide), poly(caprolactone), poly(lactide-co-caprolactone), poly(glycolide-co-caprolactone), and poly(D,L-lactide-co-glycolide-co-ε-caprolactone);
where the first therapeutic agent is triacetyl resveratrol; and
wherein a concentration of the first therapeutic agent on at least a portion of the outer surface of the expandable balloon ranges from about 1 to about 5 µg/mm$^2$.

12. The drug coated balloon catheter of claim 11, wherein the balloon outer surface comprises a polyamide block copolymer.

13. The drug coated balloon catheter of claim 12, wherein the copolymer comprising acrylate comprises about 60% by weight methyl methacrylate, 30% by weight ethyl acrylate and 10% by weight 2-trimethylammoniumethyl methacrylate chloride.

14. The drug coated balloon catheter of claim 11, wherein the first polymer is a copolymer comprising acrylate.

15. The drug coated balloon catheter of claim 11, wherein the second polymer is selected from the group consisting of poly(lactide), poly(glycolide), poly(lactide-co-glycolide), poly(caprolactone), poly(lactide-co-caprolactone), poly(glycolide-co-caprolactone), and poly(D, L-lactide-co-glycolide-co-ε-caprolactone).

16. The drug coated balloon catheter of claim 15, wherein the second polymer is a poly(lactide-co-glycolide).

17. The drug coated balloon catheter of claim 11, further comprising a second therapeutic agent, wherein the second therapeutic agent is selected from quercetin, pharmaceutically acceptable salts, and pharmaceutically acceptable derivatives thereof.

18. The drug coated balloon catheter of claim 17, wherein a concentration of the second active therapeutic agent based on the surface area of the balloon ranges from about 1 to about 5 µg/mm$^2$.

\* \* \* \* \*